US 9,232,907 B2

(12) United States Patent
Lee et al.

(10) Patent No.: US 9,232,907 B2
(45) Date of Patent: Jan. 12, 2016

(54) SYSTEM, METHOD AND COMPUTER-ACCESSIBLE MEDIUM FOR UTILIZING CARDIAC OUTPUT TO IMPROVE MEASUREMENT OF TRACER INPUT FUNCTION IN DYNAMIC CONTRAST-ENHANCED MAGNETIC RESONANCE IMAGING

(75) Inventors: Vivian S. Lee, Salt Lake City, UT (US); Henry Rusinek, Great Neck, NY (US); Lei Zhang, Salt Lake City, UT (US)

(73) Assignee: New York University, New York, NY (US)

( * ) Notice: Subject to any disclaimer, the term of this patent is extended or adjusted under 35 U.S.C. 154(b) by 524 days.

(21) Appl. No.: 13/262,228

(22) PCT Filed: Apr. 2, 2010

(86) PCT No.: PCT/US2010/029870
§ 371 (c)(1),
(2), (4) Date: Dec. 9, 2011

(87) PCT Pub. No.: WO2010/115165
PCT Pub. Date: Oct. 7, 2010

(65) Prior Publication Data
US 2012/0095328 A1 Apr. 19, 2012

Related U.S. Application Data

(60) Provisional application No. 61/166,672, filed on Apr. 3, 2009.

(51) Int. Cl.
*A61B 5/055* (2006.01)
*A61B 5/029* (2006.01)
(Continued)

(52) U.S. Cl.
CPC ............ *A61B 5/055* (2013.01); *A61B 5/029* (2013.01); *A61B 5/0263* (2013.01);
(Continued)

(58) Field of Classification Search
CPC .. A61B 5/02755; A61B 5/0263; A61B 5/029; A61B 5/7275; A61B 5/72; A61B 5/02; A61B 5/055; G01R 33/56366; G01R 33/56308; G06T 2207/10096
USPC .......................... 600/407, 410, 420; 382/131
See application file for complete search history.

(56) References Cited

U.S. PATENT DOCUMENTS

| 7,069,068 | B1 | 6/2006 | Ostergaard |
| 7,512,435 | B2 * | 3/2009 | Wu et al. ................ 600/431 |

(Continued)

FOREIGN PATENT DOCUMENTS

WO WO2008/147921 * 4/2008

OTHER PUBLICATIONS

Mahnken et al., "Measurement of cardiac output from a test-bolus injection in multislice computed tomography", Eur. Radiol., Apr. 16, 2003, pp. 2498-2504.*

(Continued)

*Primary Examiner* — Katherine Fernandez
(74) *Attorney, Agent, or Firm* — Andrews Kurth LLP

(57) ABSTRACT

Exemplary embodiments of method, system and computer-accessible medium according to the present disclosure can be provided for converting magnetic resonance (MR) arterial signal intensity versus time curves to arterial input functions (AIF) with less susceptibility to artifacts such as flow-related enhancement. Exemplary methods, systems and computer-accessible medium can be used to constrain AIF to satisfies the indicator dilution principle, according to which the area under an initial pass component of AIF can be equal to the injected dose divided by the cardiac output. For example, Monte Carlo simulations of MR renography and tumor perfusion protocols can be performed for comparison with conventional methods.

27 Claims, 11 Drawing Sheets

(51) Int. Cl.
*A61B 5/026* (2006.01)
*A61B 5/0275* (2006.01)
*A61B 5/02* (2006.01)
*A61B 5/00* (2006.01)
*G01R 33/563* (2006.01)

(52) U.S. Cl.
CPC .............. *A61B 5/02755* (2013.01); *A61B 5/02* (2013.01); *A61B 5/72* (2013.01); *G01R 33/56308* (2013.01); *G01R 33/56366* (2013.01); *G06T 2207/10096* (2013.01)

(56) References Cited

U.S. PATENT DOCUMENTS 8,197,437 B2 * 6/2012 Kalafut et al. .................. 604/67
2003/0211036 A1 11/2003 Degani et al.
2008/0125643 A1 5/2008 Huisman et al.

OTHER PUBLICATIONS

International Search Report for PCT/US2010/029870 mailed Oct. 19, 2010.
International Written Opinion for PCT/US2010/029870 mailed Oct. 19, 2010.

* cited by examiner

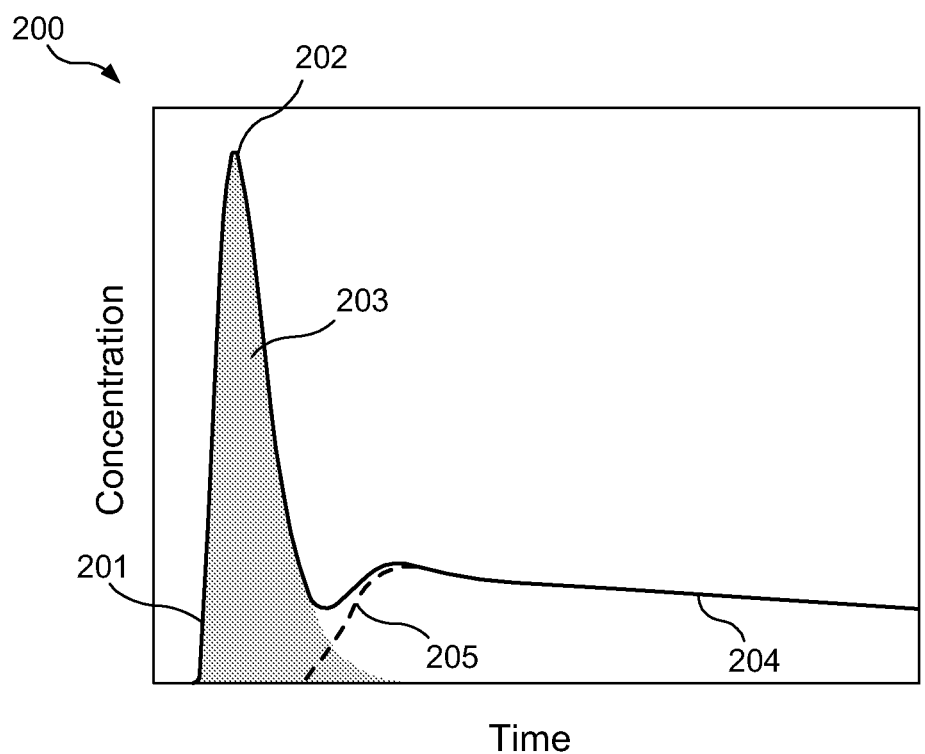
F I G. 2

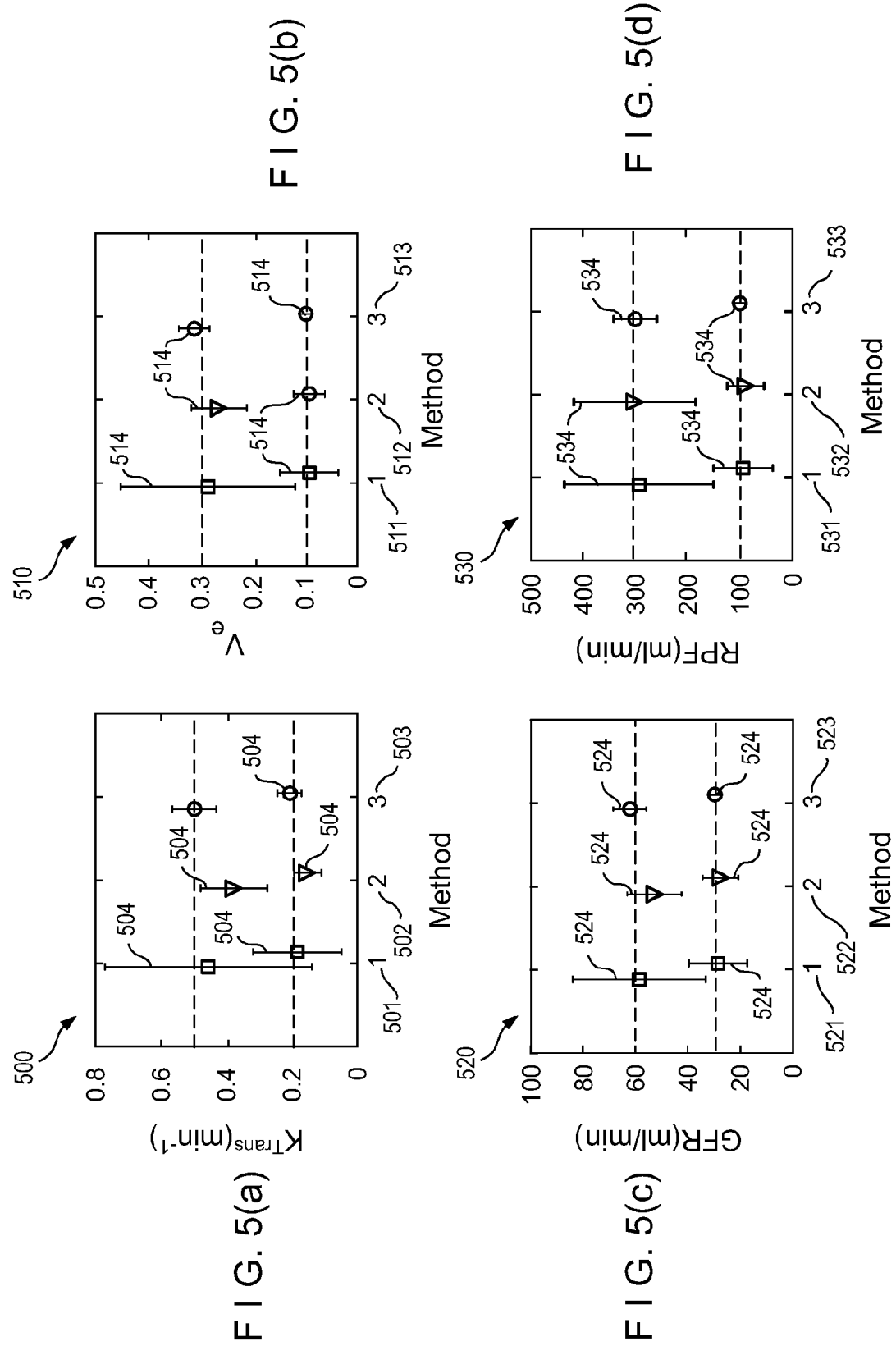

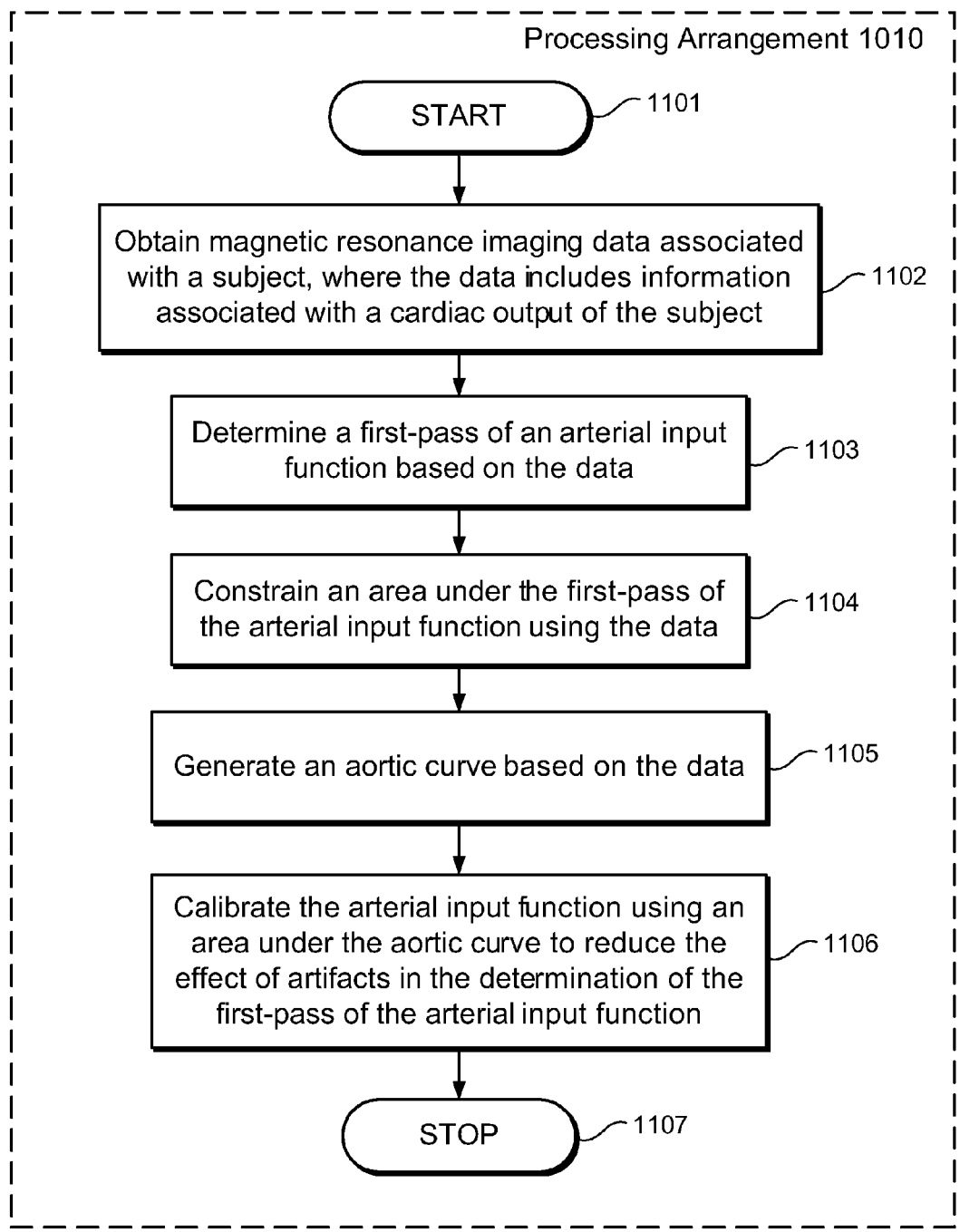
F I G. 11

SYSTEM, METHOD AND COMPUTER-ACCESSIBLE MEDIUM FOR UTILIZING CARDIAC OUTPUT TO IMPROVE MEASUREMENT OF TRACER INPUT FUNCTION IN DYNAMIC CONTRAST-ENHANCED MAGNETIC RESONANCE IMAGING

CROSS-REFERENCE TO RELATED APPLICATION(S)

The present application relates to and claims priority from International Patent Application No. PCT/US2010/028924 filed on Apr. 2, 2010, and from U.S. Patent Application No. 61/166,672 filed Apr. 3, 2009, the entire disclosures of which are hereby incorporated herein by reference.

STATEMENT REGARDING FEDERALLY SPONSORED RESEARCH

The present disclosure was developed, at least in part, using Government support under Contract Grant No. DK-063183 awarded by the National Institute of Diabetes and Digestive and Kidney Diseases, and Contract No. DK-061599 awarded by the National Institute of Diabetes and Digestive and Kidney Diseases. Therefore, the Federal Government may have certain rights in the invention.

FIELD OF THE DISCLOSURE

The present disclosure relates generally to exemplary embodiments of systems, methods and computer-accessible media for performing dynamic contrast-enhanced magnetic resonance imaging (DCE-MRI) procedure(s), and more particularly, to a performance of DCE-MRI procedure(s) to measure a transit of a tracer such as a gadolinium-chelate to estimate physiologic parameters such as perfusion or permeability in vivo, for example.

BACKGROUND INFORMATION

Dynamic contrast-enhanced magnetic resonance imaging (DCE-MRI) procedure(s) can measure the transit of a tracer such as a gadolinium-chelate to estimate physiologic parameters such as perfusion or permeability in vivo. Applications of DCE-MRI procedure(s) can include estimates of tumor angiogenesis (see, e.g., Barrett T. et al., *MRI of tumor angiogenesis*, J Magn Reson Imaging, 26(2):235-249 (2007), and Kiessling F. et al., *Contrast agents and applications to assess tumor angiogenesis in vivo by magnetic resonance imaging*, Current medicinal chemistry, 14(1):77-91 (2007)), and response to therapy (see, e.g., Turnbull L. W., *Dynamic contrast-enhanced MRI in the diagnosis and management of breast cancer*. NMR in biomedicine (2008), and Marcus C. D. et al., *Imaging techniques to evaluate the response to treatment in oncology: Current standards and perspectives*. Critical reviews in oncology/hematology (2008), as well as physiologic measurements of organ function such as kidney glomerular filtration rates and perfusion (see, e.g., Lee V. S. et al., *Renal Function Measurements from MR Renography and a Simplified Multicompartmental Model*, Am J Physiol Renal Physiol, 292: F1548-1559 (2007); Zhang J. L., et al., *Functional assessment of the kidney from magnetic resonance and computed tomography renography: impulse retention approach to a multicompartment model*, Magn Reson Med; 59(2):278-288 (2008); Hackstein N., et al., *Glomerular filtration rate measured using the Patlak plot technique and contrast-enhanced dynamic MRI with different amounts of gadolinium-DTPA*, J Magn Reson Imaging; 22(3):406-414 (2005)). Performance can use a direct, well-controlled injection of the tracer bolus into the feeding vessel. Observed tissue concentration versus time curves can then reflect regional/local perfusion, permeability, or volume fraction, with minimal confounding effects due to the shape of the input function. However, for practical reasons, tracers can typically be injected intravenously, which can resulting in unpredictable dilution and/or widening of the bolus by the time it arrives at the feeding vessels, for example. Therefore, accurate quantitative analysis of DCE-MRI data can involve an individually measured arterial input function (AIF). Reliable measurement of AIF can be important to, e.g., the precision of determining the function of organ or tumor (see, e.g., Roberts C., et al., *Comparison of errors associated with single- and multi-bolus injection protocols in low-temporal-resolution dynamic contrast-enhanced tracer kinetic analysis*, Magn Reson Med; 56(3):611-619 (2006); Wang Y., et al., *Feasibility of using limited-population-based arterial input function for pharmacokinetic modeling of osteosarcoma dynamic contrast-enhanced MRI data*, Magn Reson Med; 59(5):1183-1189 (2008); Peeters F., et al., *Inflow correction of hepatic perfusion measurements using T1-weighted, fast gradient-echo, contrast-enhanced MRI*, Magn Reson Med; 51(4):710-717 (2004)).

There can be several challenges to determine AIF. First, a relationship between MR signal intensity and a gadolinium concentration can be nonlinear, and can even be non-monotonic (see, e.g., Bokacheva L., et al., *Quantitative determination of Gd-DTPA concentration in T(1)-weighted MR renography studies*, Magn Reson Med; 57(6):1012-1018 (2007); Materne R., et al., *Assessment of hepatic perfusion parameters with dynamic MRI*, Magn Reson Med; 47(1):135-142 (2002)). Second, MR signal measurements from a blood vessel can be distorted by multiple artifacts, including, e.g., inflow effect (see, e.g., Peeters F., et al., *Inflow correction of hepatic perfusion measurements using T1-weighted, fast gradient-echo, contrast-enhanced MRI*, Magn Reson Med; 51(4):710-717 (2004); Ivancevic M. K., et al., *Inflow effect correction in fast gradient-echo perfusion imaging*, Magn Reson Med; 50(5):885-891 (2003)), dephasing (see, e.g., Heilmann M., et al., *Simultaneous dynamic T1 and T2\* measurement for AIF assessment combined with DCE MRI in a mouse tumor model*, Magma (New York, N.Y.; 20(4):193-203 (2007), $B_1$ inhomogeneity (see, e.g., Wang J., et al., *Factors influencing flip angle mapping in MRI: RF pulse shape, slice-select gradients, off-resonance excitation, and B0 inhomogeneities*, Magn Reson Med; 56(2):463-468 (2006); Warntjes J. B., et al., *Novel method for rapid, simultaneous T1, T\*2, and proton density quantification*, Magn Reson Med; 57(3):528-537 (2007); Wang J., et al., *T1 measurements incorporating flip angle calibration and correction in vivo*, J Magn Reson; 182(2):283-292 (2006), Cheng H. L., et al., *Rapid high-resolution T(1) mapping by variable flip angles: accurate and precise measurements in the presence of radiofrequency field inhomogeneity*, Magn Reson Med; 55(3):566-574 (2006); van der Schaaf I., et al., *Influence of partial volume on venous output and arterial input function*, Ajnr; 27(1):46-50 (2006)), partial volume effect, (see, e.g., van der Schaaf I., et al., *Influence of partial volume on venous output and arterial input function*, Ajnr; 27(1):46-50 (2006); Chen J. J., et al., *Partial volume effect in quantitative magnetic resonance perfusion imaging*, Conf Proc IEEE Eng Med Biol Soc; 2:1132-1135 (2004)), and effects of flow pulsatility and turbulence.

Different approaches have been described to compute tracer concentration C(t). What can be considered to be a simple approach can be one that estimates concentration as being proportional to normalized signal intensity, e.g.:

$$C(t)=k[S(t)-S(0)]/S(0) \quad [1]$$

where S can be the MRI signal intensity, S(0) can be the signal intensity before contrast enhancement, and k can be a calibration constant (see, e.g., Wen J. G., et al., *Evaluation of renal function in normal and hydronephrotic kidneys in rats using gadolinium diethylenetetramine-pentaacetic acid enhanced dynamic magnetic resonance imaging*, The Journal of urology; 163(4):1264-1270 (2000); Jones R. A., et al., *Dynamic contrast-enhanced MR urography in the evaluation of pediatric hydronephrosis: Part 1, functional assessment*, AJR Am J Roentgenol; 185(6):1598-1607 (2005)). The use of this approach can be desired when combined with the use of low doses of contrast, due to an approximate linearity of the relationship between S(t) and C(t) for commonly used gradient echo acquisition sequences and C(t)<0.7 mM (see, e.g., Bokacheva L., et al., *Quantitative determination of Gd-DTPA concentration in T(1)-weighted MR renography studies*, Magn Reson Med; 57(6):1012-1018 (2007)). Alternatively, C(t) can be estimated from the longitudinal relaxation time $T_1(t)$. The estimation of $T_1$ from signal intensity can usually be nonlinear and it can require the knowledge of S(0) and $T_1$ (see, e.g., Bokacheva L., et al., *Quantitative determination of Gd-DTPA concentration in T(1)-weighted MR renography studies*, Magn Reson Med; 57(6):1012-1018 (2007); Bokacheva L., et al., *Single breath-hold T1 measurement using low flip angle TrueFISP*, Magn Reson Med; 55(5): 1186-1190 (2006)). This approach (which can be called, e.g., a direct conversion) can be applicable to a wider range of C(t), and can yield accuracy better than approximately 10% in solid tissues (e.g., liver, kidneys, muscle) (see, e.g., Bokacheva L., et al., *Quantitative determination of Gd-DTPA concentration in T(1)-weighted MR renography studies*, Magn Reson Med; 57(6):1012-1018 (2007)). However, it can be significantly less accurate in the aorta and/or other major arteries, e.g., in regions used for measurement of AIF. A MR signal from these arteries can be subject to artifacts listed herein above, and signal errors can be further amplified when estimating tracer concentration by direct conversion, for example.

In an attempt to minimize the adverse effect of AIF distortions, Parker et al. (see, e.g., Parker G. J., et al., *Experimentally-derived functional form for a population-averaged high-temporal-resolution arterial input function for dynamic contrast-enhanced MRI*, Magn Reson Med; 56(5):993-1000 (2006)) and Wang et al. (see, e.g., Wang Y., et al., *Feasibility of using limited-population-based arterial input function for pharmacokinetic modeling of osteosarcoma dynamic contrast-enhanced MRI data*, Magn Reson Med; 59(5):1183-1189 (2008)) described that it is possible to average AIFs obtained from a group of controls and derived by direct conversion from measured signal intensities. For the analysis of patient data, rather than use actual patient AIFs, the population averaged AIF can be used instead. A rationale of averaging multiple AIFs can be to reduce random, uncorrelated sources of errors. However, systematic artifacts (such as inflow and partial volume effect) can likely distort the signals in a similar way across all individuals, preventing cancellation of these sources, for example. Moreover, the magnitude and the shape of AIF can depend on a patient's status (such as cardiac output and blood volume) and on the injection protocol used with the patient (see, e.g., Le Sech C., et al., *Determination of pulmonary mean transit time and cardiac output using a one-dimensional model*, Bulletin of mathematical biology; 58(6):1155-1170 (1996); Reiser U. J., *Study of bolus geometry after intravenous contrast medium injection: dynamic and quantitative measurements (Chronogram) using an X-ray CT device*, Journal of computer assisted tomography; 8(2):251-262 (1984); Hany T. F., et al., *Optimization of contrast timing for breath-hold three-dimensional MR angiography*, J Magn Reson Imaging; 7(3):551-556 (1997); Boos M., et al., *Arterial first pass gadolinium-CM dynamics as a function of several intravenous saline flush and Gd volumes*, J Magn Reson Imaging; 13(4):568-576 (2001)). For example, by disregarding differences between patients and/or protocols, the use of an averaged AIF can introduce additional sources of errors.

Thus, it may be beneficial to address and/or overcome at least some of the deficiencies described herein above.

SUMMARY OF EXEMPLARY EMBODIMENTS OF THE DISCLOSURE

Indeed, one of the objects of certain exemplary embodiments of the present disclosure can be to address the exemplary problems described herein above, and/or to overcome the exemplary deficiencies commonly associated with the prior art as, e.g., described herein.

Accordingly, the present disclosure describes exemplary embodiments that can be used to compute AIF using a constrained conversion procedure that can take into account, e.g., the subject's (e.g., patient's) cardiac output. Because the constrained procedure can force an area under the peak of AIF to obey the theory of indicator dilution, the resulting perfusion parameters can be more robust than, e.g., the direct and averaged methods. Exemplary measurements of, e.g., (a) tumor perfusion and/or (b) renal filtration as well as of a test-retest DCE-MRI analysis of MR renography, can be provided, and comparison of exemplary methods according to the present disclosure with conventional approaches may be facilitated, for example.

For example, provided and described herein are certain exemplary embodiments of exemplary system, method and computer-accessible medium in accordance with the present disclosure which can be used for generating tracer concentration data associated with a structure. A structure, as used herein, can include, without being limited to a subject and/or one or more anatomical structures of the subject, including, e.g., a subject's entire heart, peripheral venous, the right heart, pulmonary system, the left heart, and peripheral arterial compartments, etc.

According to one exemplary embodiment of the present disclosure, computer-accessible medium can be provided that can have instructions thereon for generating tracer concentration data associated with a structure. When a computing arrangement executes the instructions, the computing arrangement can be configured to, e.g., modify time sequence signal data so that, when converted to tracer concentration data, the resulting concentration data satisfies the indicator dilution principle. The computing arrangement can be further configured to identify a first pass component of signal information, and wherein the resulting concentration data satisfies the indicator dilution principle within the first pass component of signal information. The computing arrangement can be further configured to generate a baseline signal level at least in part based on a first pass component of signal data/curve, for example.

Additionally, the computing arrangement can be further configured to generate time sequence concentration data as a function of (i) time sequence signal data, (ii) the baseline signal level, or (iii) cardiac output data. The time sequence concentration data can be generated to satisfies a constraint based on the indicator dilution principle. The computing arrangement can be further configured to obtain an initial time sequence signal data pertaining to the structure from a particular source, and the generation of the time sequence concentration data can be performed by modifying the initial time sequence signal data as a function of the generated baseline signal level in accordance with certain exemplary embodiments of the present disclosure.

The computing arrangement can be further configured to obtain and utilize further data associated with a cardiac output of the structure from a further source that is different than the particular source. For example, the computing arrangement can be further configured to obtain the initial time sequence signal data from a blood vessel, which can be an artery.

The baseline signal level can be determined based on (i) an area under the curve corresponding to the tracer concentration data associated with the first pass signal data, (ii) a mass of a tracer injected into the structure, and (iii) the cardiac output data. The time sequence concentration data can be generated as a function of the baseline signal level, the time sequence signal data, and the cardiac output data. Further, the time sequence signal data can be generated based on data associated with a region of interest pertaining to an artery using dynamic contrast enhanced MRI data. Additionally, the generation of the time sequence concentration data can be performed using a indicator dilution principle.

The computing arrangement can be further configured to determine the first pass component of signal curve by, e.g., fitting time sequence signal data to a gamma variate function. The computing arrangement can be further configured to generate the time sequence data, and the generation of the time sequence signal data can include shifting values of the time sequence signal data. The time sequence signal data can be converted to tracer concentration data using, e.g., a direct measurement method. The tracer concentration data corresponds to an arterial input function. The time sequence signal data can be generated based on radiological data, such as MRI, CT, SPECT, and/or PET data. For example, the time sequence signal data can be generated based on data associated with a region of interest pertaining to a blood vessel.

In certain exemplary embodiments according to the present disclosure, provided is a method for generating tracer concentration data associated with a structure, comprising for modifying time sequence signal data so that, when converted to tracer concentration data, the resulting concentration data satisfies the indicator dilution principle. In addition to the above procedures, an exemplary embodiment of a method according to the present disclosure can further comprising at least one of displaying or storing the tracer concentration data in a storage arrangement in at least one of a user-accessible format or a user-readable format.

Additionally, according to certain exemplary embodiments of the present disclosure, provided here is an exemplary system for generating tracer concentration data associated with a structure, which can include a computer-accessible medium having executable instructions thereon. When at least one computing arrangement executes the instructions, the computing arrangement(s) can be configured to modify time sequence signal data so that, when converted to tracer concentration data, the resulting concentration data satisfies the indicator dilution principle. The computing arrangement can be further configured identify a first pass component of signal information, and wherein the resulting concentration data satisfies the indicator dilution principle within the first pass component of signal information, for example.

Further, also in accordance with certain exemplary embodiments of the present disclosure, provided herein is a computer-accessible medium having instructions thereon for generating tracer concentration data associated with a structure, where, when a computing arrangement executes the instructions, the computing arrangement can be configured to obtain time sequence signal information, identify a first pass component of the time sequence signal information, modify the time sequence signal information as a function of the first pass component of the time sequence signal information and cardiac output data, and generate the tracer concentration data using the modified time sequence signal information. The computing arrangement can be further configured to generate time sequence concentration data as a function of, e.g., (i) time sequence signal data, (ii) a baseline signal level, and (iii) cardiac output data. For example, the time sequence concentration data can be generated to satisfies a constraint based on the indicator dilution principle.

The exemplary computing arrangement can be further configured to obtain an initial time sequence signal data pertaining to the structure from a particular source, and the generation of the time sequence concentration data can be performed by modifying the initial time sequence signal data as a function of a baseline signal level. Further, the computing arrangement can be configured to obtain and utilize further data associated with a cardiac output of the structure from a further source that is different than the particular source.

These and other objects, features and advantages of the present disclosure will become apparent upon reading the following detailed description of exemplary embodiments of the present disclosure, when taken in conjunction with the accompanying exemplary drawings and appended claims.

BRIEF DESCRIPTION OF THE DRAWINGS

The foregoing and other objects of the present disclosure will be apparent upon consideration of the following detailed description, taken in conjunction with the accompanying exemplary drawings and claims showing illustrative embodiments of the invention, in which:

FIG. 2 is an illustration of an exemplary graph of concentration versus time, in accordance with certain exemplary embodiments of the present disclosure;

FIGS. 5(a)-5(d) are illustrations of exemplary graphs showing a comparison of parameter determinations using different input procedures, in accordance with certain exemplary embodiments of the present disclosure;

FIG. 11 is flow diagram of a method for generating tracer concentration data associated with a structure, in accordance with certain exemplary embodiments of the present disclosure.

Figure 1:
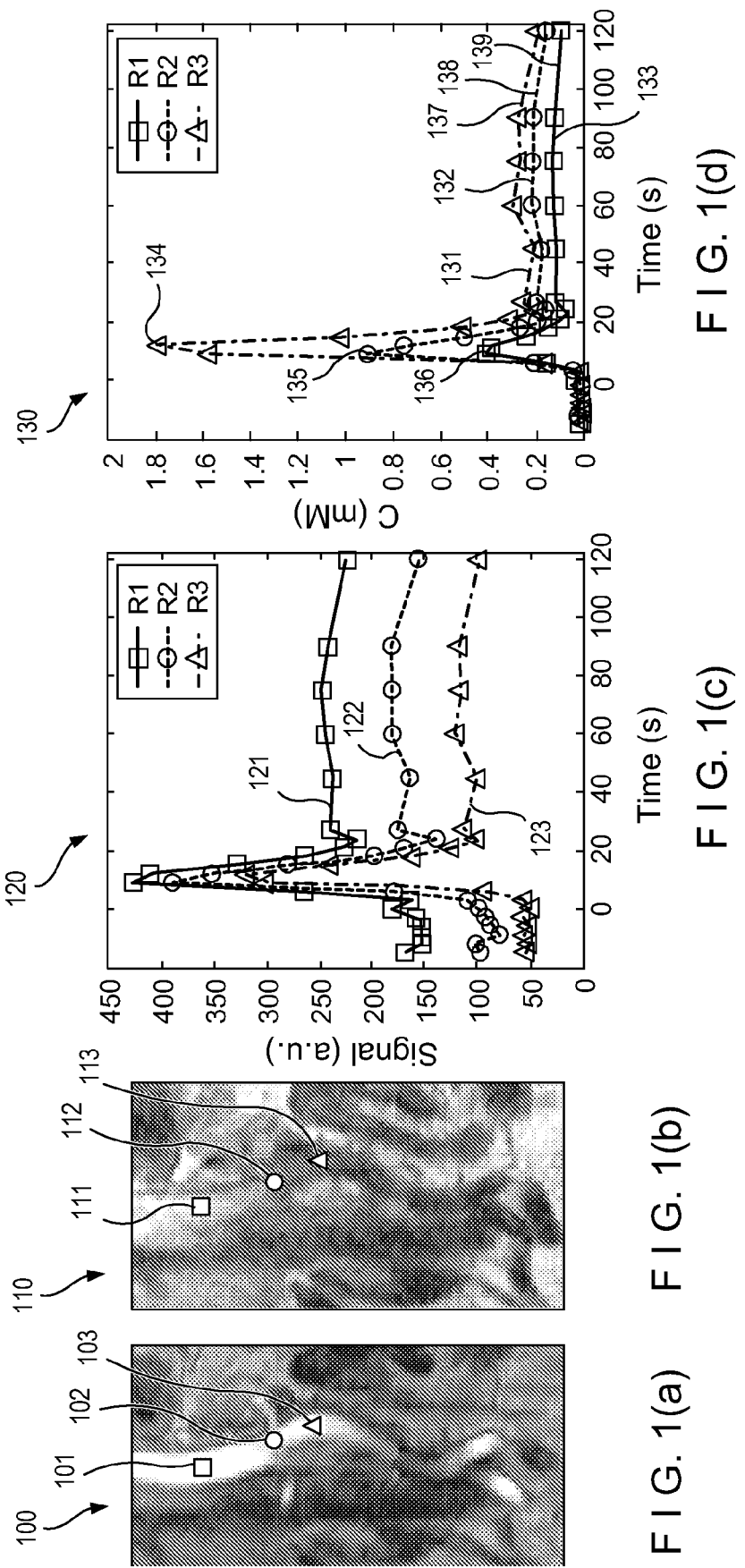
FIG. 1(a) is an exemplary cropped post-contrast image showing regions of interest (ROIs) at different levels of aorta to demonstrate a variability in an aortic input function by direct measurement, in accordance with certain exemplary embodiments of the present disclosure.
FIG. 1(b) is a cropped precontrast image showing inflow effect in an upper level of aorta, according to an exemplary embodiment of the present disclosure.
FIG. 1(c) is an illustration of an exemplary graph of signal intensity versus time curves sampled from three regions shows different baseline levels that can be due to an inflow effect, according to an exemplary embodiment of the present disclosure.
FIG. 1(d) is an illustration of an exemplary graph of concentration versus time curves by direct measurement, which results can be due to the different baseline levels shown in FIG. 1(c)

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described embodiments without departing from the true scope and spirit of the subject disclosure.

DETAILED DESCRIPTION OF EXEMPLARY
EMBODIMENTS OF THE DISCLOSURE

Exemplary Materials and Methods

Exemplary Conversion from MR Signal to Tracer Concentration

In certain exemplary embodiments according to the present disclosure, the quantification of tracer concentration can involve measuring a change in longitudinal relaxation time $T_1$ due to $T_1$-shortening effect of the tracer. For example, contrast concentration C can be proportional to the change in relaxation rate $1/T_1$, e.g., $$C(t) = [1/T_1(t) - 1/T_1(0)]/r_1, \quad [2]$$

where $r_1$ can be the specific relaxivity of the contrast agent.

$T_1(t)$ can be estimated from an analytical relationship between signal intensity (S) and longitudinal relaxation time ($T_1$). This relationship can involve sequence parameters such as, e.g., flip angle α, repetition time TR, scaling factor relating to spin density, system gain, coil sensitivity, etc. (see, e.g., Bokacheva L., et al., *Quantitative determination of Gd-DTPA concentration in T(1)-weighted MR renography studies*, Magn Reson Med; 57(6):1012-1018 (2007)). For example, for a spoiled gradient recalled echo (SPGR) sequence, which can be widely used for dynamic imaging, $$S(t) = M_0 \sin\alpha \frac{1 - e^{-TR/T_1(t)}}{1 - e^{-TR/T_1(t)} \cos\alpha}, \quad [3]$$

where $M_0$ can represent an exemplary equilibrium that can magnetization and the other system gain factors. In addition, given pre-contrast (t≤0) values S(0) and $T_1(0)$, $M_0$ can be determined from known system parameters and substituted back into Eq. [3], allowing $T_1(t)$ to be expressed as:

$$T_1(t) = TR \Big/ \ln\left(\frac{w - vu\cos\alpha}{w - vu}\right), \quad [4]$$

where $v = S(t)/S(0)$, $u = 1 - e^{-TR/T_1(0)}$ and $w = 1 - \cos\alpha e^{-TR/T_1(0)}$. Substituting $T_1(t)$ in Eq. [2] results in tracer concentration that corresponds to each acquired signal (30):

$$C(t) = \frac{1}{r_1 TR}\left[\ln\left(\frac{w - vu\cos\alpha}{w - vu}\right) - \frac{TR}{T_1(0)}\right]. \quad [5]$$

This exemplary method to obtain AIF can be referred to as direct conversion.

Calculation of tracer concentration using Eq. [5] may need to use a knowledge of flip angle, TR, $T_1(0)$ and S(0). Possible errors in these values combine to inaccurate concentration estimates.

Exemplary Normalization of an Input Function Using Cardiac Output

An exemplary approach in accordance with the present disclosure can utilize an indicator dilution (e.g., Stewart-Hamilton) principle (31) to constrain the area under AIF. For example, after a bolus injection, an arterial concentration can display an initial peak, characteristic of the "first pass" (e.g., initial pass) of the tracer, followed by a lower recirculation tail. In an imaginary system with no recirculation, AIF can consist of only the first-pass (initial pass) component.

The indicator dilution (or, e.g., Stewart-Hamilton) principle (see, e.g., Zierler K. L., *Equations for Measuring Blood Flow by External Monitoring of Radioisotopes*, Circ Res; 16:309-321 (1965). ** indicates that $$D = Q \times AUC, \quad [6]$$

where AUC can be the area under a "first pass" concentration curve, D can be the mass of the injected tracer, and Q can be the cardiac output, defined as the volume of blood being pumped by the heart per minute. Eq. [6] can be valid for AIF sampled anywhere in the body. As the sampling site moves to more distal locations, the shape of AIF can become flatter due to tracer dispersion, without changing the area under the "first pass" component (see, e.g., Millard R. K., *Indicator-dilution dispersion models and cardiac output computing methods*, The American journal of physiology; 272(4 Pt 2):H2004-2012 (1997)).

Because the precision of the direct conversion from DCE-MRI signal to concentration can be poor, the indicator dilution method may be not suitable for estimation of Q. However, if Q can be assumed or measured independently, its value can be used to improve the conversion in accordance with exemplary embodiments of the present disclosure.

The traditional "gold standard" thermo dilution method for measurement of Q may require an insertion of a pulmonary artery catheter. However, many noninvasive alternative techniques are becoming available and are gaining increasing acceptance (see, e.g., Rebergen S. A., et al., *Magnetic resonance measurement of velocity and flow: technique, validation, and cardiovascular applications*, American heart journal; 126(6):1439-1456 (1993); Berton C., et al., *Equipment review: new techniques for cardiac output measurement—oesophageal Doppler, Fick principle using carbon dioxide, and pulse contour analysis*, Critical care (London, England); 6(3):216-221 (2002); Szolar D. H., et al., *Cardiovascular applications of magnetic resonance flow and velocity measurements*, J Magn Reson Imaging; 6(1):78-89 (1996)). Measurement of cardiac output by MRI can be routinely used as a part of clinical cardiac MRI examinations (see, e.g., Kuehne T., et al., *Magnetic resonance imaging guided catheterisation for assessment of pulmonary vascular resistance: in vivo validation and clinical application in patients with pulmonary hypertension*, Heart (British Cardiac Society); 91(8):1064-1069 (2005); Pennell D. J., et al., *Clinical indications for cardiovascular magnetic resonance (CMR): Consensus Panel report*, Eur Heart J; 25(21):1940-1965 (2004)). In particular, Q can be measured rapidly using velocity-encoded phase contrast MRI with less than 10% error (see, e.g., Rebergen S. A., et al., *Magnetic resonance measurement of velocity and flow: technique, validation, and cardiovascular applications*, American heart journal; 126(6):1439-1456 (1993); Szolar D. H., et al., *Cardiovascular applications of magnetic resonance flow and velocity measurements*, J Magn Reson Imaging; 6(1):78-89 (1996)).

Exemplary Implementation of AIF Normalization

We now describe an exemplary embodiment according to the present disclosure for utilizing Q to derive an arterial input function. The exemplary process can consist of three steps S1-S3, for example:

S1. Fit the signal versus time curve by gamma variate function to obtain the first-pass signal curve $S_{fp}$ (i.e. eliminate recirculation) (see, e.g., Davenport, R., *The derivation of the gamma-variate relationship for tracer dilution curves*, J Nucl Med; 24(10):945-948 (1983)).

$$S_{fp}(t) = S_0 + A \cdot (t-t_0)^a e^{-(t-t_0)/b}, \quad [7]$$

where $S_0$ can be the baseline (pre-contrast) signal level, $t_0$ can be time delay, and A, a and b are the parameters controlling the shape of gamma variate function.

S2. Adjust the pre-contrast signal $S_0$ to a new value ($S_0^{opt}$) so that the converted concentration $C_{fp}$ has the expected area under curve, e.g., $$\int_0^\infty C_{fp}(t) dt = D/Q. \quad [8]$$

Appendix A indicates that that, according to some exemplary embodiments of the present disclosure, fixed values A, a and b in Eq. [7], AUC of the converted $C_{fp}$ can be a monotonic function of $S_0$. Because of this property, a unique $S_0^{opt}$ can be found for virtually any AUC predicted by Stewart-Hamilton principle.

S3. Shift the whole signal versus time curve S(t) to the new baseline level $S_0^{opt}$, and convert it to concentration using Eq. [3-5].

Exemplary Simulations

Monte Carlo simulations can be performed to evaluate the performance of exemplary methods according to the present disclosure in dynamic MR renography and in MR tumor perfusion imaging, and/or to compare it with direct conversion and the previously published averaged input approach (see, e.g., Wang Y., et al., *Feasibility of using limited-population-based arterial input function for pharmacokinetic modeling of osteosarcoma dynamic contrast-enhanced MRI data*, Magn Reson Med; 59(5):1183-1189 (2008).

An exemplary AIF can be generated by a compartmental model that was proposed by Bae et al. (see, e.g., Bae K. T., et al., *Aortic and hepatic contrast medium enhancement at CT. Part II. Effect of reduced cardiac output in a porcine model*, Radiology, 207(3):657-662 (1998); Bae K. T., *Peak contrast enhancement in CT and MR angiography: when does it occur and why? Pharmacokinetic study in a porcine model*, Radiology; 227(3):809-816 (2003)) for describing the transit of intravascular tracer in human body. To simulate a random distribution of patients, flow rates and compartment volumes of the model can be randomly selected within, e.g., approximately ±30% range around their mean values (e.g., as used in the example of section B herein below). For a given contrast injection protocol, AIF can be derived as the output from the left-heart compartment. Realistic injection protocols (see, e.g., Exemplary Table 1) can be used to simulate tumor perfusion and kidney function applications.

The simulated signal intensity versus time curve can be constructed from each ideal AIF using Equations [2] and [3], with pre-defined parameter values, e.g.: TR=2.3 ms, $\alpha=9°$, $T_1(0)=1200$ ms (see, e.g., Stanisz G. J., et al., *T1, T2 relaxation and magnetization transfer in tissue at 3T*, Magn Reson Med; 54(3):507-512 (2005), S(0)=50, $r_1$=4.3 mM$^{-1}$ s$^{-1}$ (see, e.g., Rohrer M., et al., *Comparison of magnetic properties of MRI contrast media solutions at different magnetic field strengths*, Invest Radiol; 40(11):715-724 (2005), and time interval=3 s. Zero-mean Gaussian noise with standard deviation 10% of S(0) can be added to each signal point, to simulate random noise in MR signal. The signal curve can be also shifted vertically with a shift randomly chosen within a conservative ±30% range of S(0), reflecting the artifacts due to inflow, dephasing and partial volume effects seen clinically.

Certain exemplary methods can be used to obtain AIF, such as, e.g.: (a) direct conversion, (b) an exemplary method according to the present disclosure, and (c) the averaged input function that can be constructed separately using Bae's model. For both the direct conversion procedure and the exemplary method according to the present disclosure, the simulated signal intensity versus time curve can be converted to a concentration versus time curve.

For a direct conversion, the flip angle can be randomly chosen, e.g., within ±1° range of true flip angle, to reflect the difference between the true and the nominal flip angles due to $B_1$ inhomogeneity (see, e.g., Warntjes J. B., et al., *Novel method for rapid, simultaneous T1, T*2, and proton density quantification*, Magn Reson Med; 57(3):528-537 (2007)). For example, approximately five percent random noise can be added to $T_1(0)$ (see, e.g., Cheng H. L., *T1 measurement of flowing blood and arterial input function determination for quantitative 3D T1-weighted DCE-MRI*, J Magn Reson Imaging; 25(5):1073-1078 (2007)). Pre-contrast signal S(0) can be obtained by averaging, e.g., 5 pre-contrast signals generated by the Monte Carlo simulation. With the exemplary methods according to the present disclosure, random noise can be added to cardiac output to reflect its measurement error. (See, e.g., Rebergen S. A., et al., *A. Magnetic resonance measurement of velocity and flow: technique, validation, and cardiovascular applications*, American heart journal; 126(6):1439-1456 (1993); Kuehne T., et al., *Magnetic resonance imaging guided catheterisation for assessment of pulmonary vascular resistance: in vivo validation and clinical application in patients with pulmonary hypertension*, Heart (British Cardiac Society); 91(8):1064-1069 (2005)).

With an exemplary averaged input function approach (see, e.g., Wang Y., et al., *Feasibility of using limited-population-based arterial input function for pharmacokinetic modeling of osteosarcoma dynamic contrast-enhanced MRI data*, Magn Reson Med; 59(5):1183-1189 (2008); Parker G. J., et al., *Experimentally-derived functional form for a population-averaged high-temporal-resolution arterial input function for dynamic contrast-enhanced MRI*, Magn Reson Med; 56(5):993-1000 (2006)); e.g., one hundred AIFs simulating arterial inputs from 100 different patients can be generated by the compartmental model (see, e.g., Bae K. T., *Peak contrast enhancement in CT and MR angiography: when does it occur and why? Pharmacokinetic study in a porcine model*, Radiology; 227(3):809-816 (2003); Robert P., et al., *Optimization of a blood pool contrast agent injection protocol for MR angiography*, J Magn Reson Imaging; 21(5):611-619 (2005)) (See, e.g., Appendix B), and can be subject to the same process of noise addition and direct conversion as above. These simulated AIFs can be shifted in time to ensure that the peaks occurred at the same time point, and then can be averaged to obtain the averaged AIF. (See, e.g., Parker G. J., et al., *Experimentally-derived functional form for a population-averaged high-temporal-resolution arterial input function for dynamic contrast-enhanced MRI*, Magn Reson Med; 56(5): 993-1000 (2006)).

For tumor simulation, a well known model by Tofts et al see, e.g., Tofts P. S., *Modeling tracer kinetics in dynamic Gd-DTPA MR imaging*, J Magn Reson Imaging; 7(1):91-101 (1997)) with transfer constant $K^{trans}$ and extracellular extravascular volume $v_e$ can be employed. Representative high-perfusion and low-perfusion values (see, e.g., Exemplary Table 1) can be taken from the literature (see, e.g., Padhani A. R., et al., *Reproducibility of quantitative dynamic MRI of normal human tissues*, NMR in biomedicine; 15(2): 143-153 (2002); Stevenson J. P., et al., *Phase I trial of the antivascular agent combretastatin A4 phosphate on a 5-day schedule to patients with cancer: magnetic resonance imaging evidence for altered tumor blood flow*, J Clin Oncol; 21(23):4428-4438 (2003); Galbraith S. M., et al., *Combretastatin A4 phosphate has tumor antivascular activity in rat and man as demonstrated by dynamic magnetic resonance imaging*, J Clin Oncol; 21(15):2831-2842 (2003); Hayes C., et al., *Assessing changes in tumour vascular function using dynamic contrast-enhanced magnetic resonance imaging*, NMR in biomedicine; 15(2):154-163 (2002)). For an exemplary kidney simulation, a three-compartment renal model (see, e.g., Lee V. S., et al., *Renal Function Measurements from MR Renography and a Simplified Multicompartmental Model*, Am J Physiol Renal Physiol; 292:F1548-1559 (2007); Zhang J. L., et al., *Functional assessment of the kidney from magnetic resonance and computed tomography renography: impulse retention approach to a multicompartment model*, Magn Reson Med; 59(2):278-288 (2008)) can be used. Normal and impaired kidneys can be simulated by using different values of glomerular filtration rate (GFR) and renal plasma flow (RPF). (See, e.g., Exemplary Table 1).

Random simulations can be repeated $N_{trial}$ times (e.g., $N_{trial}=2000$), to obtain $N_{trial}$ estimates for each parameter. The standard deviation (SD) of the $N_{trial}$ estimates and the difference between their average and the true value indicates the precision and the measurement bias, respectively. An exemplary two-sampled F-test can be used to compare SDs of the estimates from different methods.

In order to analyze the effect of cardiac output error on the precision of the functional parameters, a conversion of the simulated AIF by exemplary methods according to the present disclosure can be implemented by using different cardiac-output error levels, such as, e.g.: 5%, 10%, 15% and 20%, and the parameter estimates from these different AIFs can be compared.

Exemplary methods according to the present disclosure can adjust pre-contrast signal S(0) alone to constrain the converted concentration curve. Bases on exemplary prior error sensitivity analyses, such implementation can correct for errors in flip angle and $T_1(0)$. To confirm this, simulations can be repeated with random noise added to only flip angle or $T_1(0)$, with and all other parameters kept exact. Different levels of noise can be added to flip angle, with, e.g., SD=0.5, 1.0, 1.5, and 2.0 degree, and for, e.g., $T_1(0)$, SD=50, 100, 150 and 200 ms. Both the direct conversion procedure and the exemplary methods according to the present disclosure can be used for AIF conversion, and the estimates for $K^{trans}$ can be compared.

Exemplary Patient Analysis

Exemplary methods according to the present disclosure can be applied to patient data to test its ability to improve the reproducibility of MR renographic analysis. Four healthy volunteers (e.g., 2 males and 2 females, age: 29.3±1.0 years) can volunteer. The protocol can be approved by local institutional review board, and written informed consent can be obtained from all subjects. For each volunteer, three dimensional MR renography can be repeated on three separate days with the same imaging protocol, e.g.: TR 2.3 ms, TE 0.8 ms, flip angle 9°, field of view 309 mm×450 mm, matrix 100×256, slice thickness 3.0 mm, 32 slices, acquisition time 3 s. Exemplary subjects can be instructed to be npo for at least 8 hours prior to the examinations and then can be given 500 ml water to drink just prior to the study. Prior to contrast administration, five 3D images can be acquired during one 15 s breath-hold. Eight seconds following the start of a bolus injection of 4 ml Gd-DTPA (Magnevist, Berlex Laboratories, Wayne, N.J.) at 2 ml/s (followed by 20 ml saline flush), the 3D acquisitions can be repeated continuously for 30 s, during which the subject can be asked to suspend respiration as long as possible. Acquisitions can be repeated during separate 3 s breath-holds at multiple time points for, e.g., at least 10 min thereafter.

Semi-automated image registration and segmentation can be applied to the 3D renography data sets to produce aortic, renal cortical, and renal medullary signal intensity versus time curves (see, e.g., Rusinek H., et al., *Performance of an automated segmentation algorithm for 3D MR renography*, Magn Reson Med; 57(6):1159-1167 (2007)). Signal curves of renal cortex and medulla can be converted to concentration versus time curves using direct conversion described previously. $T_1$ value for renal cortex and medulla without contrast can be, e.g., 950 and 1300 ms, respectively (see, e.g., de Bazelaire C. M., et al., *MR imaging relaxation times of abdominal and pelvic tissues measured in vivo at 3.0 T: preliminary results*, Radiology; 230(3):652-659 (2004); Bluml S., et al., *Spin-lattice relaxation time measurement by means of a TurboFLASH technique*, Magn Reson Med; 30(3): 289-295 (1993)).

The conversion of the aortic signal intensity curves to concentration curves (e.g., generation of concentration curves based on the aortic signal intensity curves) can be implemented in the following exemplary ways for comparison: direct conversion, the averaged input approach, and an exemplary method according to the present disclosure. Exemplary embodiments of an implementation of the averaged input approach for these test-retest data in accordance with the present disclosure can be slightly different from its original implementation. Rather than averaging AIFs across a separate group of patients, AIFs obtained by direct conversion from the three scans for the same patient can be averaged, and the average AIF can then be applied for analysis of each individual data of the patient. For implementing exemplary methods according to the present disclosure, each AIF by direct conversion can be fitted by gamma variate function for the initial 30 seconds after tracer injection to obtain the AUC of the first (initial) pass. Averaging the AUCs for the three scans of a same patient resulted in the 'true' AUC for the patient. The true AUC can be used in the conversion of the three aortic signal curves by an exemplary method according to the present disclosure.

The concentration curve of tissues and aorta can be analyzed by a three-compartment model (see, e.g., Zhang J. L., et al., *Functional assessment of the kidney from magnetic resonance and computed tomography renography: impulse retention approach to a multicompartment model*, Magn Reson Med; 59(2):278-288 (2008)) to estimate GFR and RPF for each of the exemplary studies from the same patient. Using exemplary methods according to the present disclosure for normalizing AIF, the standard deviation (SD) of the three estimates of one parameter can be reduced, compared with the other exemplary methods.

The distribution of tumor perfusion parameters ($K^{trans}$ and $v_e$) can be estimated using different AIF methods. Exemplary methods according to the present disclosure can improve the precisions of both parameters by at least a factor of three compared with the direct method. For example, in the high-perfusion tumor simulation (e.g., nominal value $K^{trans}$=0.5 $min^{-1}$), the SD of $K^{trans}$ can be, e.g., 0.08 $min^{-1}$ using the constrained AIF versus, e.g., 0.31 $min^{-1}$ using the conventional direct conversion method. Precision improved by, e.g., a factor of 4 for $v_e$. The use of averaged AIF can also improve the precision, while not as much as the exemplary cardiac output method. In addition, the averaged AIF can be associated with a systematic deviation of computed parameters. For example, the systematic bias for high-perfusion $K^{trans}$ can be about −41% and for $v_e$ can be about −8%, whereas, the estimates by exemplary methods according to the present disclosure can show minimal deviation from their true values, e.g., approximately −4.6% for $K^{trans}$, and approximately −0.8% for $v_e$.

Similar to the results in tumor simulation, the precisions of all parameters for both normal and impaired kidneys can be significantly improved (e.g., about three-fold for GFR and three-fold for RPF) when using exemplary methods according to the present disclosure and the deviation of these estimates from their true values can be small (e.g., less than about 1 ml/min for GFR, less than about 2 ml/min for RPF).

The simulations described above can be obtained assuming the precision of cardiac output (Q) measurement of 10%. There can be a nearly linear relationship between the precision of Q and the precision of functional parameters computed using exemplary methods according to the present disclosure. For a relative error of Q=5%, for example, the CV for the parameters can be, e.g., 9%~13%, while for relative error of 20%, CV for the parameters can be, e.g., 17%~23%.

While the primary source of error in determining the AIF by the direct conversion method can be related to flow-related enhancement affecting $S_0$ measurement, other sources of error, such as $T_1(0)$ and flip angle, can also be important. Exemplary embodiments of methods according to the present disclosure can correct for errors in these terms as well. It is possible to plot a simulated precision of $K^{trans}$ computed assuming errors are restricted to flip angle (e.g., panel (a)) and $T_1(0)$ (panel (b)), with no error in $S_0$. In spite of the fact that $S_0$ alone can be corrected (see, e.g., step S2 of the new procedure), the exemplary method is able to well tolerate these other sources of errors. The conventional method, on the other hand, can be highly sensitive to inaccurate values of flip angle and $T_1(0)$.

Exemplary Volunteer Analysis

The GFR estimates in healthy volunteers on three separate days can show greater consistency using exemplary methods according to the present disclosure than the other two methods. The SDs of the three GFR estimates for, e.g., each of 8 different kidneys. SD by the exemplary method, e.g., 6.4±4.4 ml/min, can be significantly lower than that by direct conversion, e.g., 20.5±12.7 ml/min, and also significantly lower than that by the averaged input approach, 7.8±4.4 ml/min. The SD of RPF estimates by the exemplary method, 27.4±17.8 ml/min, can be lower than that by direction conversion, e.g., 97.8±32.1 ml/min, or by averaged input approach, e.g., 92.7±64.5 ml/min.

In this exemplary analysis, the exemplary embodiment of the method according to the present disclosure can be provided for converting MR signal intensity of aortic blood into tracer concentration. For example, the area under the first (initial) pass of arterial input function (AIF), which can be determined according to the indicator dilution (Stewart-Hamilton) principle, can be used to constrain the AIF and to reduce the effect of various artifacts. In our experience, the main source of error in deriving AIF can be the inaccurate baseline signal intensity, S(0), mostly resulting from inflow artifacts and which become especially pronounced when the acquisition plane may not be aligned with the direction of the flowing blood in-plane. By applying the exemplary method, the baseline, unenhanced arterial signal intensity level can be corrected and ensure that the first-pass component of the corrected AIF has the correct area under curve and thus the correct magnitude.

The performance of the exemplary methods according to the present disclosure can be evaluated using Monte Carlo simulations and with volunteer data. In the Monte Carlo simulations, the physiologic parameters of kidney filtration and tumor perfusion can be estimated with three-fold higher precision than the estimates by direct conversion. The precision of the parameters using the exemplary method can be reduced from, e.g., about 30% to approximately 10%. These exemplary values can be further improved with more precise measurement of cardiac output. A volunteer analysis for measuring renal function can be used to confirm the ability of the exemplary method to reduce variability in DCE MRI measurements.

Several methods have been described to correct for the MR artifacts. To correct for the inflow effect, Ivancevic et al. (see, e.g., Ivancevic M. K., et al., *Inflow effect correction in fast gradient-echo perfusion imaging*, Magn Reson Med; 50(5): 885-891 (2003)) developed a calibration method based on flow phantoms, and Peeters et al. (see, e.g., Peeters F., et al., *Inflow correction of hepatic perfusion measurements using T1-weighted, fast gradient-echo, contrast-enhanced MRI*, Magn Reson Med; 51(4):710-717 (2004)) derived an analytical model describing flow-related enhancement. To account for dephasing effects, Heilmann et al. (see, e.g., Heilmann M., et al., *Simultaneous dynamic T1 and T2\* measurement for AIF assessment combined with DCE MRI in a mouse tumor model*, Magma (New York, N.Y.; 20(4):193-203 (2007)) applied saturation-recovery multi-gradient-echo snapshot technique to simultaneously measure $T_1$ and $T_2$\* in a dynamic protocol. Roberts et al (see, e.g., Roberts C., et al., *Comparison of errors associated with single- and multi-bolus injection protocols in low-temporal-resolution dynamic contrast-enhanced tracer kinetic analysis*, Magn Reson Med; 56(3): 611-619 (2006)) designed a double-injection method to reduce the sampling error. Unlike these conventional methods that deal with one specific artifact, the exemplary methods according to the present disclosure can be effective in reducing errors from several sources, including flip angle and $T_1(0)$ errors.

The exemplary averaged input approach can be used to reduce the overall effect of the various artifacts. However, averaging may not necessarily cancel the systematic artifacts such as inflow and partial volume effects. In addition, assuming a same AIF for different patients can be valid when the patient population is homogeneous. This assumption may not apply in most clinical settings and when dealing with patients of unknown status. The averaged input approach can result in a low accuracy of the perfusion parameters, with, e.g., about 15%~28% deviation in RPF and, e.g., about 35%~40% deviation in $K^{trans}$. Perfusion parameters can be highly sensitive to errors in the first-pass peak (see, e.g., Zhang J. L., et al., *Functional assessment of the kidney from magnetic resonance and computed tomography renography: impulse retention approach to a multicompartment model*, Magn Reson Med; 59(2):278-288 (2008)).

Several features of exemplary embodiments of the methods according to the present disclosure can provide certain advantages over the previous methods. For example, first, the AIF can be calibrated (e.g., calculated, determined, normalized, adjusted, etc.) using the area under the first-pass (e.g., initial pass) aortic curve, which can be calculated for each individual patient. Second, the estimate of high concentration in the first-pass peak can be more sensitive to MR artifacts than low concentration in the tail. As a consequence, calibration of AUC for the first-pass peak corrects most of the AIF error. Third, as discussed herein, more than one source of artifacts can be corrected.

Because they can significantly improve reproducibility, the exemplary embodiments of the methods according to the present disclosure can be valuable in applications where repeated measurements are compared, for example, in the monitoring of tumor response to therapy, or pharmacologic challenge such as angiotensin-converting enzyme inhibitor-enhanced renography. These exemplary interventions can typically have a subtle effect on physiologic parameters. For example, ACE inhibitor induces approximately 10% decrease in GFR in patients with renovascular hypertension (see, e.g., Taylor A. T., et al., *Procedure guideline for diagnosis of renovascular hypertension*. Society of Nuclear Medicine. J Nucl Med; 39(7):1297-1302 (1998)). A detection of subtle changes may require high reproducibility of the measurements. In our volunteer study, the proposed method improved the precision of GFR from, e.g., 20.5±12.7 ml/min to 6.4±4.4 ml/min. The measurement of cardiac output may not be necessary, provided that cardiac output change across serial DCE-MRI exams can be neglected.

Exemplary embodiments of the system, method and computer-accessible medium according to the present disclosure can be used in other clinical DCE MRI applications and with larger groups of patients, for example. Various exemplary embodiments of the system, method and computer-accessible medium according to the present disclosure can also be used to develop relatively quick and accurate cardiac output measures within the same imaging session as DCE-MRI.

Certain exemplary embodiments of the methods according to the present disclosure can overcome the effect of artifacts when estimating AIF from MR data, for example. Simulations and analysis involving human volunteers can illustrate that exemplary methods according to the present disclosure can significantly improve the ability to measure functional parameters in MR renography and in tumor perfusion measurements. Improved reproducibility can be especially useful for applications where repeated measurements are to be compared.

A: Exemplary AUC of a First-Pass Component ($C_{FP}$) as a Strictly Monotonic Function of $S_0$ A definition of AUC and its partial derivative with respect to $S_0$ can be expressed as $$AUC = \int_0^\infty C_{fp}(t)\,dt \text{ and } \frac{\partial AUC}{\partial S_0} = \int_0^\infty \left[\frac{\partial C_{fp}}{\partial S_0}\right]dt. \quad [A1]$$

The partial derivative of tracer concentration with respect to $S_0$ can be $$\frac{\partial C}{\partial S_0} = \frac{\partial C}{\partial v}\frac{\partial v}{\partial S_0} = \left[\frac{1}{r_1 TR}\frac{uw(1-\cos\alpha)}{(w-vu\cos\alpha)(w-vu)}\right]\left[(-1)\frac{S}{S_0^2}\right], \quad [A2]$$

where $v=S(t)/S_0$, $u=1^+e^{-TR/T_1(0)}$ and $w=1-\cos\alpha e^{-TR/T_1(0)}$. Since $\partial C/\partial S_0$ is negative, $\partial AUC/\partial S_0$ is also negative. As a consequence AUC is a monotonic function of $S_0$. With this property, a unique $S_0$ can be found for predicted AUCs.

B: Exemplary Whole-Body Tracer Kinetic Model

The exemplary Monte Carlo simulation can involve a construction of an ideal AIF, which can be achieved by using a whole body compartmental model of intravascular tracer (see, e.g., Bae K. T., et al., *Aortic and hepatic contrast medium enhancement at CT. Part II. Effect of reduced cardiac output in a porcine model*. Radiology; 207(3):657-662 (1998); Bae K. T., *Peak contrast enhancement in CT and MR angiography: when does it occur and why? Pharmacokinetic study in a porcine model*, Radiology; 227(3):809-816 (2003), for example. This exemplary model can include peripheral venous, the right heart, pulmonary system, the left heart, and peripheral arterial compartments. The exemplary model can be described by a set of differential equations based on mass conservation for each compartment:

$$\begin{cases} V_v dC_v/dt = Q_c(t)C_c - Q_v C_v(t) \\ V_r dC_r/dt = Q_v(t)C_v - Q_r C_r(t) + (1-f)Q_s C_s(t) \\ V_p dC_p/dt = Q_r(t)C_r - Q_p C_p(t) \\ V_l dC_l/dt = Q_p(t)C_p - Q_l C_l(t) \\ V_s dC_s/dt = Q_l(t)C_l - Q_s C_s(t) \end{cases} \quad [B1]$$

where $V_v$, $V_r$, $V_p$, $V_l$, $V_s$ are respectively the volume of venous, right heart, pulmonary, left heart and systemic compartments. $C_v$, $C_r$, $C_p$, $C_l$, $C_s$ are the respective concentration of venous, right heart, pulmonary, left heart and systemic compartments, and $Q_v$, $Q_r$, $Q_p$, $Q_l$, $Q_s$ represent the flows out of each compartment. $Q_c$, and $C_c$ represent the injection flow rate and concentration of the tracer. Parameter f denotes the rate of tracer elimination from human body, mainly due to renal excretion. Typical values for the parameters can be, e.g.: $V_v=40$ mL, $V_r=250$ mL, $V_p=450$ mL, $V_l=250$ mL, $V_s=5000$ mL; $Q_v=250$ mL/min, $Q_r=Q_p=Q_l=Q_s=5000$ mL/min; f=0.2 (see, e.g., Bae K. T., et al., *Aortic and hepatic contrast medium enhancement at CT. Part II. Effect of reduced cardiac output in a porcine model,* Radiology; 207(3):657-662 (1998); Bae K. T., *Peak contrast enhancement in CT and MR angiography: when does it occur and why? Pharmacokinetic study in a porcine model*, Radiology; 227(3):809-816 (2003)). A system-circulation delay, 24 s, can be included for recirculation (see, e.g., Brandfonbrener M., et al., *Changes in cardiac output with age*, Circulation; 12(4):557-566 (1955)). For simulating AIF for different patients, the flow rates and compartment volumes can be randomly chosen from, e.g., ±30% range around their typical values.

C: Example of how Exemplary Correction of AUC can Provide Accurate Estimation and/or Determination of Tracer Kinetic Parameters In general, the exemplary relationship between the dynamic data and a tracer kinetic model can be expressed as the following convolution form, $$V_t \cdot C_t(t) = F \cdot \int_0^t C_a(\tau) \cdot R(t-\tau) d\tau, \quad [C1]$$

where $V_t$ is the volume of tissue region of interest (ROI), $C_t$ the averaged concentration of tracer within tissue ROI, F blood flow, $C_a$ arterial input function (AIF), and R the impulse residue function (IRF).

A convolution, as a mathematical operation, can have a property that the area (or integral along time axis) under a convolution is the product of the areas under the two factors. Hence, $$\int_0^\infty V_t \cdot C_t(t) dt = F \int_0^\infty C_a(t) dt \cdot \int_0^\infty R(t) dt. \quad [C2]$$

On the other hand, $C_a$ can be expressed as the sum of its sequential passes (blood pumped out of heart comes back to heart, and then is pumped again and again), $$C_a(t) = C_{a1}(t) + C_{a2}(t) + C_{a3}(t) + \ldots \quad [C3]$$

where $C_{a1}$ is the first pass of AIF. Integrating both sides of equation [C3] can yields $$\int_0^\infty C_a(t) dt = \int_0^\infty C_{a1}(t) dt + \int_0^\infty C_{a2}(t) dt + \int_0^\infty C_{a3}(t) dt + \ldots \quad [C4]$$

Denoting the area under $C_{a1}$ as AUC, the area under the second pass can be smaller than AUC, expressed as f·AUC (f<1), due to tracer excretion and possible absorption during the first (initial) pass. If the rate of tracer excretion and absorption is constant, the area under the third pass can be expressed as $f^2$·AUC, and that of the fourth pass as $f^3$·AUC, so on and so forth. Equation [C4] can thus be rewritten as $$\int_0^\infty C_a(t) dt = AUC(1 + f + f^2 + f^3 + \ldots) = AUC/(1-f). \quad [C5]$$

Substituting equation [C5] in equation [C2] can yield $$\int_0^\infty V_t \cdot C_t(t) dt = \frac{AUC}{1-f} \cdot F \cdot \int_0^\infty R(t) dt \quad [C6]$$

According to the knowledge of tracer kinetics, the vascular volume in the tissue ($v_1$) can be written as $$v_1 = F \cdot \int_0^\infty R(t) dt \quad [C7]$$

Substituting equation [C7] into equation [C6] can yield $$v_1 = \frac{1-f}{AUC} \cdot \int_0^\infty V_t \cdot C_t(t) dt. \quad [C8]$$

According to equation [C8], if AIF is corrected in a way that its AUC becomes accurate, this correction method can make the estimate of vascular volume accurate. Exemplary methods according to the present disclosure of AIF correction can perform such exemplary procedure such that it facilitates an accurate estimation of a tissue vascular volume.

Exemplary parameter values for simulating tracer kinetics in various tissues.

EXEMPLARY TABLE 1

| Application | Tracer Injection | Tissue type | Parameters |
|---|---|---|---|
| Tumor | 10 ml (500 mM) at 4 ml/s | High perfusion | $K^{trans}$ = 0.5 min$^{-1}$, $v_e$ = 0.3 |
| | | Low perfusion | $K^{trans}$ = 0.2 min$^{-1}$, $v_e$ = 0.1 |
| Kidney | 4 ml (500 mM) at 2 ml/s | Normal | GFR = 60 ml/min, RPF = 300 ml/min |
| | | Impaired | GFR = 30 ml/min, RPF = 100 ml/min |

FIGS. 1(a)-1(d) are illustrations of an example to demonstrate a variability in an aortic input function by direct measurement.

Turning to FIG. 1(a), for example, this drawing shows an exemplary cropped post-contrast image 100 showing regions of interest (ROIs) 102, 103, 104 at different levels of aorta, e.g., above renal-artery level (101), at renal-artery level (102), below renal-artery level (103). ROIs 101, 102, 103 can be placed on multiple slices and centered on aortic lumen. Because of the tortuous vessel, some partial volume effect can be unavoidable.

FIG. 1(b) shows an exemplary cropped precontrast image 110 indicating an inflow effect in an upper level of an aorta.

FIG. 1(c) shows an exemplary graph 120 of signal intensity versus time curves 121, 122, 123 sampled from three regions shows different baseline levels that can be due to an inflow effect.

FIG. 1(d) shows an exemplary graph 130 of concentration versus time curves 131, 132, 133 by direct measurement, which results can be due to the different baseline levels shown in FIG. 1(c). As shown in FIG. 1(d), peaks 134, 135, 136 of concentration curves 131, 132, 133 can vary from one another (e.g., from approximately 0.4 mM (peak 136) to approximately 1.8 mM (peak 134). Further, tails 137, 138, 139 of curves 131, 132, 133, respectively, can also vary from one another (e.g., from approximately 0.1 mM (tail 139) to approximately 0.3 mM (tail 137).

FIG. 2 shows an exemplary graph 200 of concentration versus time. As shown in FIG. 2, after an intravenous bolus, the arterial input, represented by a solid line 201 can have an initial sharp peak 202, reflecting a first (initial) pass of the injected tracer, represented by an area 203, followed by a tail 204, which can be due to tracer recirculation, represented by a dashed line 205.

Figure 3:
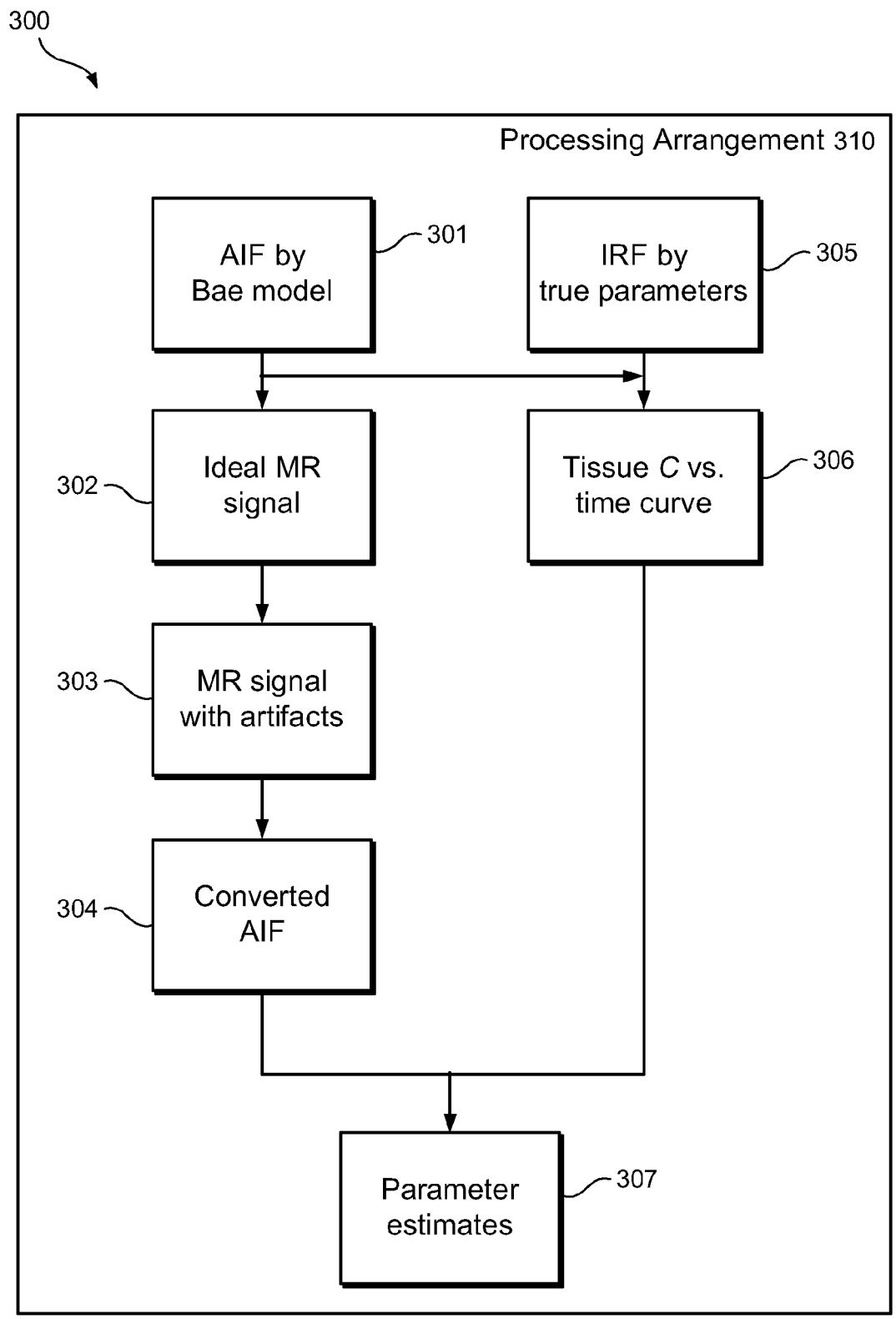
FIG. 3 is an illustration of an exemplary flow diagram of a Monte Carlo simulation of a single individual of an exemplary procedure, in accordance with certain exemplary embodiments of the present disclosure.

FIG. 3 is shows an exemplary embodiment of a flow diagram 300 of a Monte Carlo simulation of a single individual of an exemplary procedure in accordance with the present disclosure. In this example, AIF means arterial input function, IRF means impulse retention function, and C means concentration. With the use of a processing or computing arrangement 310, an exemplary AIF can be constructed by Bae's model in subprocess 301. In subprocess 302, the processing arrangement 310 can convert the exemplary AIF into a MR signal time course. The processing arrangement 310 control other devices to and/or on its own add noise to the signal and related parameters in subprocess 303 to simulate MR artifacts. In subprocess 304, the signals with artifact can be converted back to AIF (e.g., by the processing arrangement 310) using direct conversion and/or exemplary procedures in accordance with the present disclosure. In subprocess 305, the exemplary AIF can also be convolved with an IRF characterizing functional status of, e.g., tumor and/or kidney, resulting in the processing arrangement 310 possibly generating a tissue concentration versus time curve in subprocess 306. In subprocess 307, functional parameter estimates can be obtained by analyzing the converted AIF and the tissue concentration versus time curve using model-based deconvolution. For example, according to certain exemplary embodiments of the present disclosure, parameter estimates can be compared (e.g., by the processing arrangement 310) with true parameter values to assess reliability of different AIF procedures.

Figure 4:
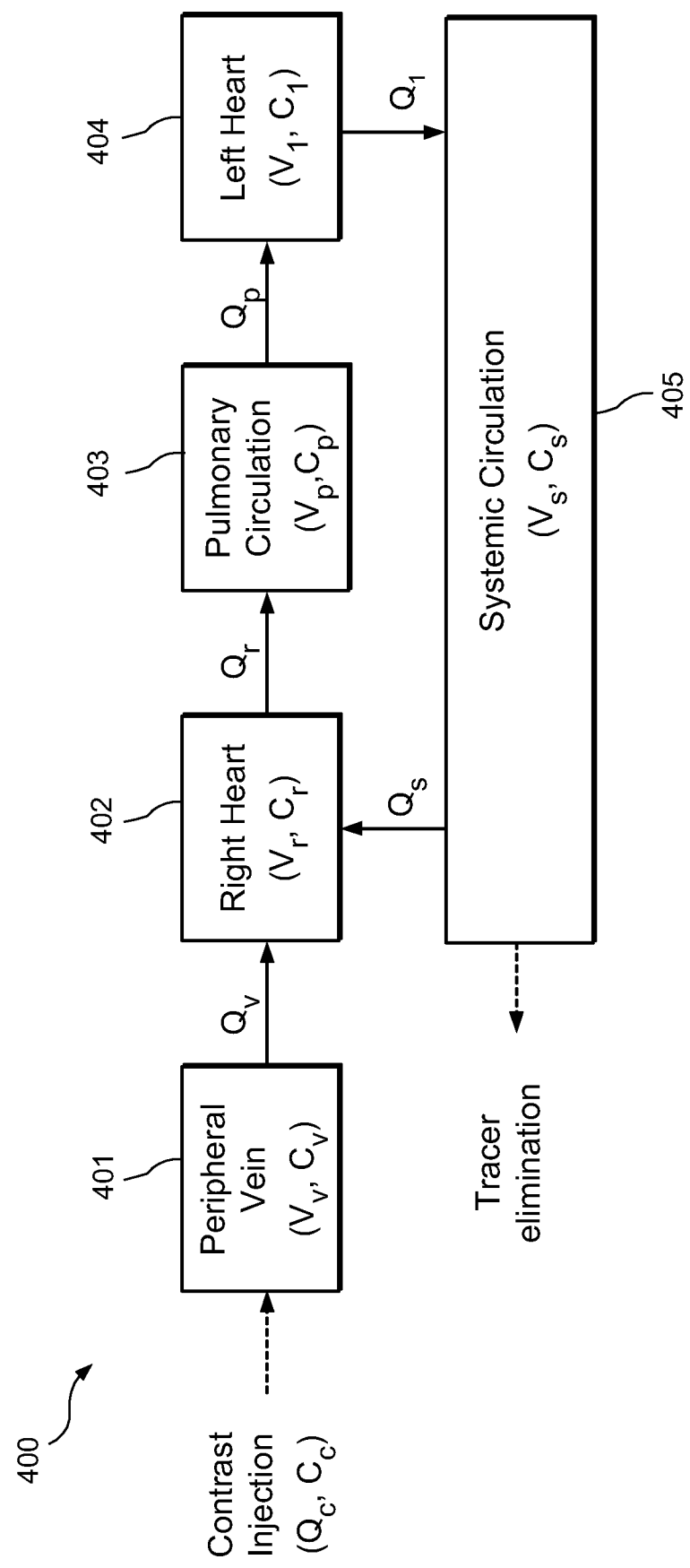
FIG. 4 is an illustration of a flow diagram of an exemplary procedure executed by a processor, in accordance with certain exemplary embodiments of the present disclosure.
Figure 6A:
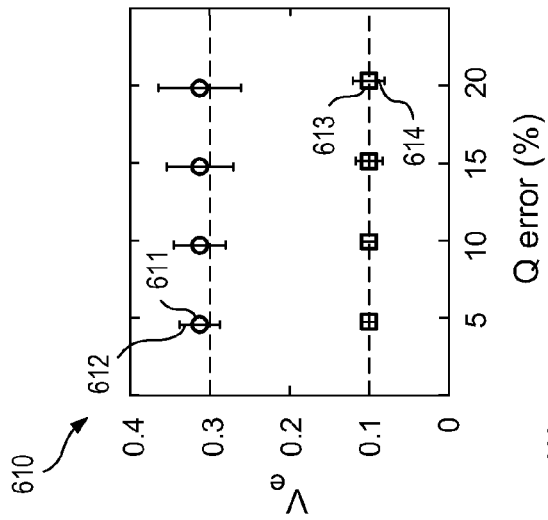
FIGS. 6(a)-6(d) are illustrations of exemplary graphs showing an exemplary effect of measurement error in cardiac output on the determinations of certain parameters when using an exemplary procedure in accordance with certain exemplary embodiments of the present disclosure.
Figure 6B:
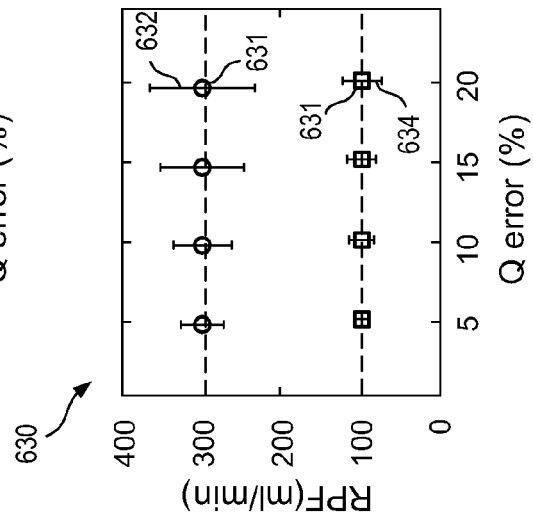
Figure 6C:
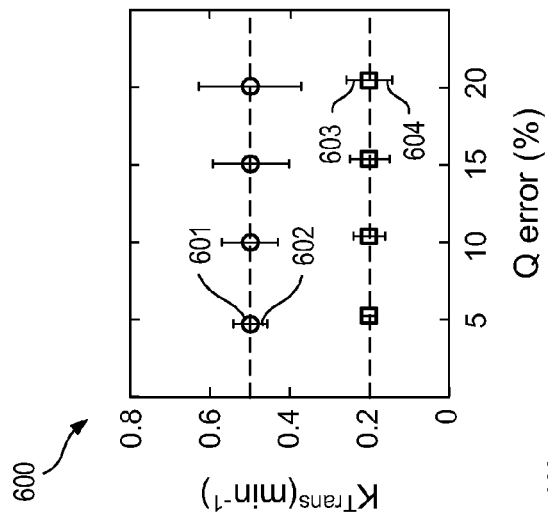
Figure 6D:
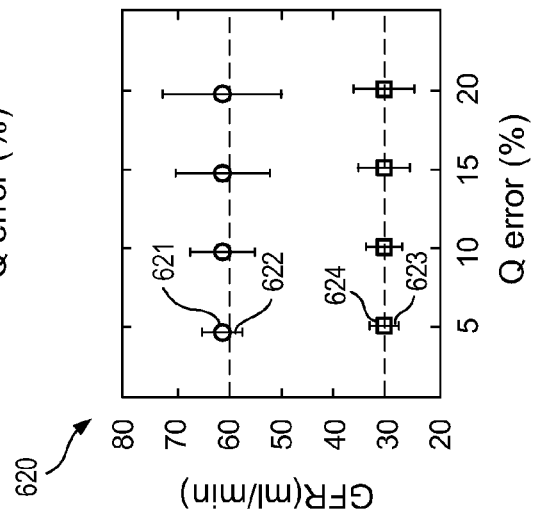

FIG. 4 shows a flow diagram 400 of an exemplary compartmental procedure according to an exemplary embodiment of the present disclosure that can be used for indicating a dynamic distribution of an intravascular tracer in a human body, which can be based on a model from Bae et al. (See, e.g., Bae K. T., et al., *Aortic and hepatic contrast medium enhancement at CT. Part II. Effect of reduced cardiac output in a porcine model*, Radiology; 207(3):657-662 (1998)). In subprocess 401, a tracer with concentration $C_c$ can be injected into a peripheral vein (volume $V_v$, tracer concentration $C_v$) with an injection flow rate $Q_c$. The tracer can then transit through the right heart ($V_r$, $C_r$) in subprocess 402, pulmonary circulation ($V_p$, $C_p$) in subprocess 403, the left heart ($V_l$, $C_l$) in subprocess 404, and system circulation ($V_s$, $C_s$) in subprocess 405. A portion of the tracer can be eliminated from systemic circulation during every pass. Exemplary values for the parameters can be as described herein above in section B, for example.

FIGS. 5(a)-5(d) show exemplary graphs 500, 510, 520, 530, respectively, which illustrate a comparison of parameter estimates by different input procedures. For example, FIG. 5(a) shows exemplary parameter estimates for an exemplary input procedure of $K^{trans}$. FIG. 5(b) shows exemplary parameter estimates of $v_e$ from a simulated MR tumor imaging procedure. FIG. 5(c) shows exemplary parameter estimates of GFR. FIG. 5(d) shows exemplary parameter estimates of RPF from a simulated MR renography procedure. In this example, estimates for procedure 1 (e.g., elements 501, 511, 521, 531) can be from a direct conversion procedure. Estimates for procedure 2 (e.g., elements 502, 512, 522, 532) can be from an averaged input procedure. Estimates for procedure 3 (e.g., elements 503, 513, 523, 533) can be from an exemplary procedure in accordance with the present disclosure. Bars 504, 514, 524, 534 can represent the standard deviations of the parameters.

FIGS. 6(a)-6(d) show exemplary graphs 600, 610, 620, 630, respectively, that show an exemplary effect of measurement error in cardiac output (Q) on the determinations of $K^{trans}$, $v_e$, GFR and RPF, respectively, when using an exemplary procedure in accordance with the present disclosure. Circles 601, 611, 621, 631 can represent determinations for high perfusion and/or normal renal function. Squares 603, 613, 623, 633 can represent determinations for low perfusion and/or impaired renal function. Bars 602, 604, 612, 614, 622, 624, 632, 634 can represent the standard deviations of the parameters.

Figure 7B:
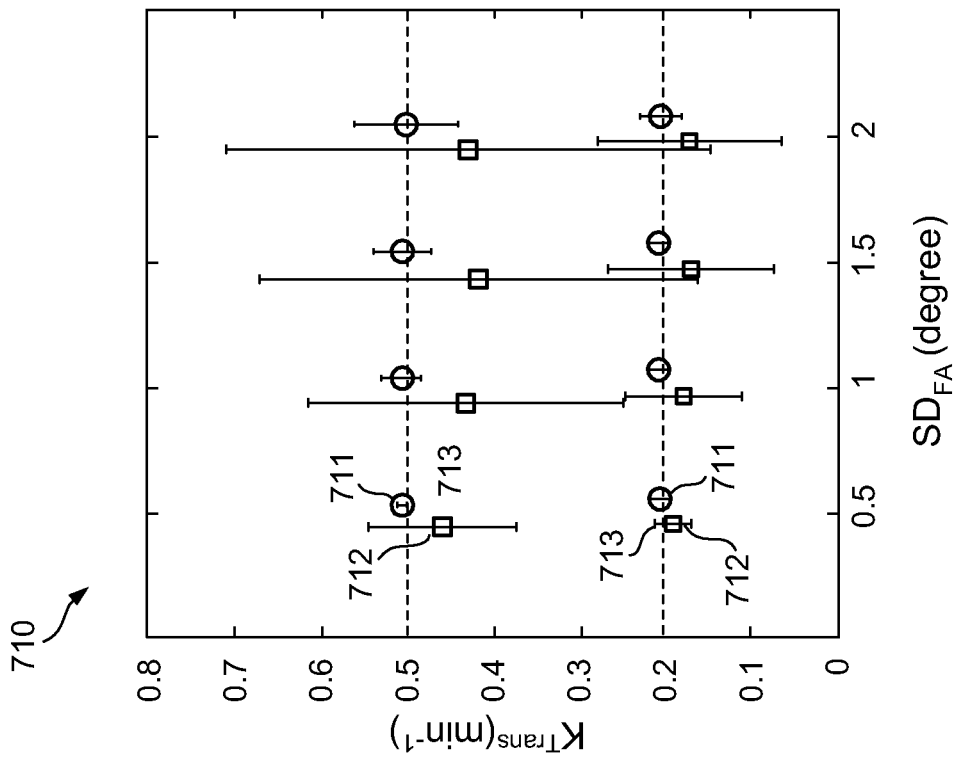
FIGS. 7(a) and 7(b) are illustrations of exemplary graphs showing a performance of exemplary procedures to correct for error of measurements and/or determinations, in accordance with certain exemplary embodiments of the present disclosure.
Figure 7A:
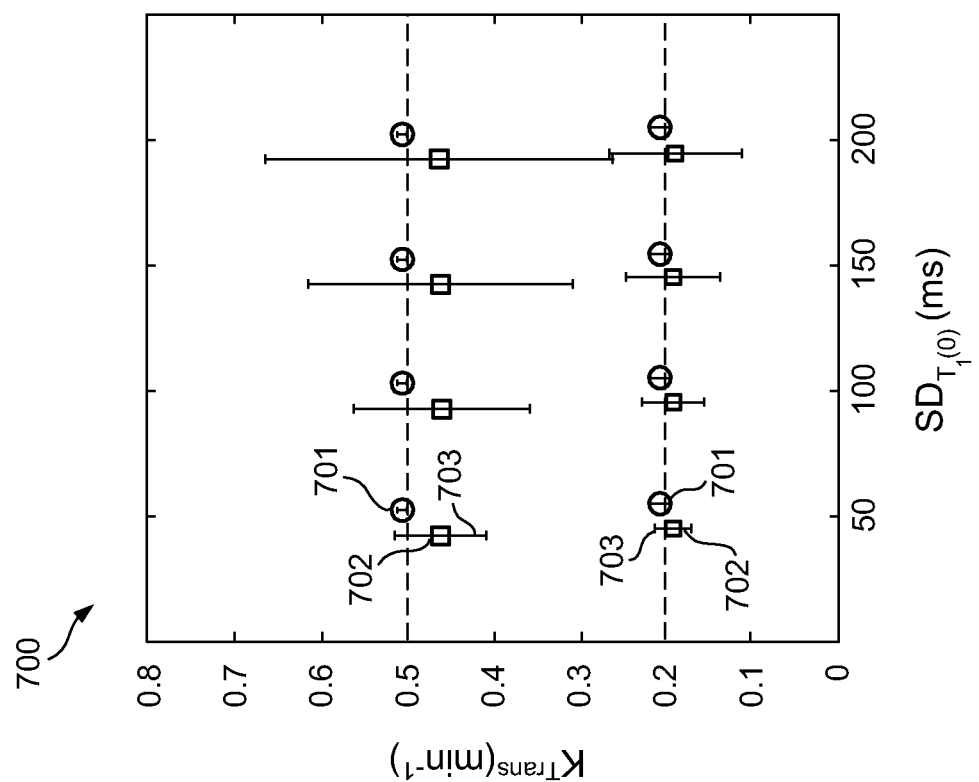

FIGS. 7(a) and 7(b) show exemplary graphs illustrating a performance of exemplary procedures according to the present disclosure in correcting for errors. In particular, FIG. 7(a) shows exemplary results for $T_1(0)$, and FIG. 7(b) for flip angle (FA). Circles 701, 711 represent determinations of $K^{trans}$ by an exemplary procedure in accordance with the present disclosure. Squares 702, 712 represent determinations by use of a direct conversion procedure. Bars 703, 713 represent standard deviations of $K^{trans}$.

Figures 8A, 8B:
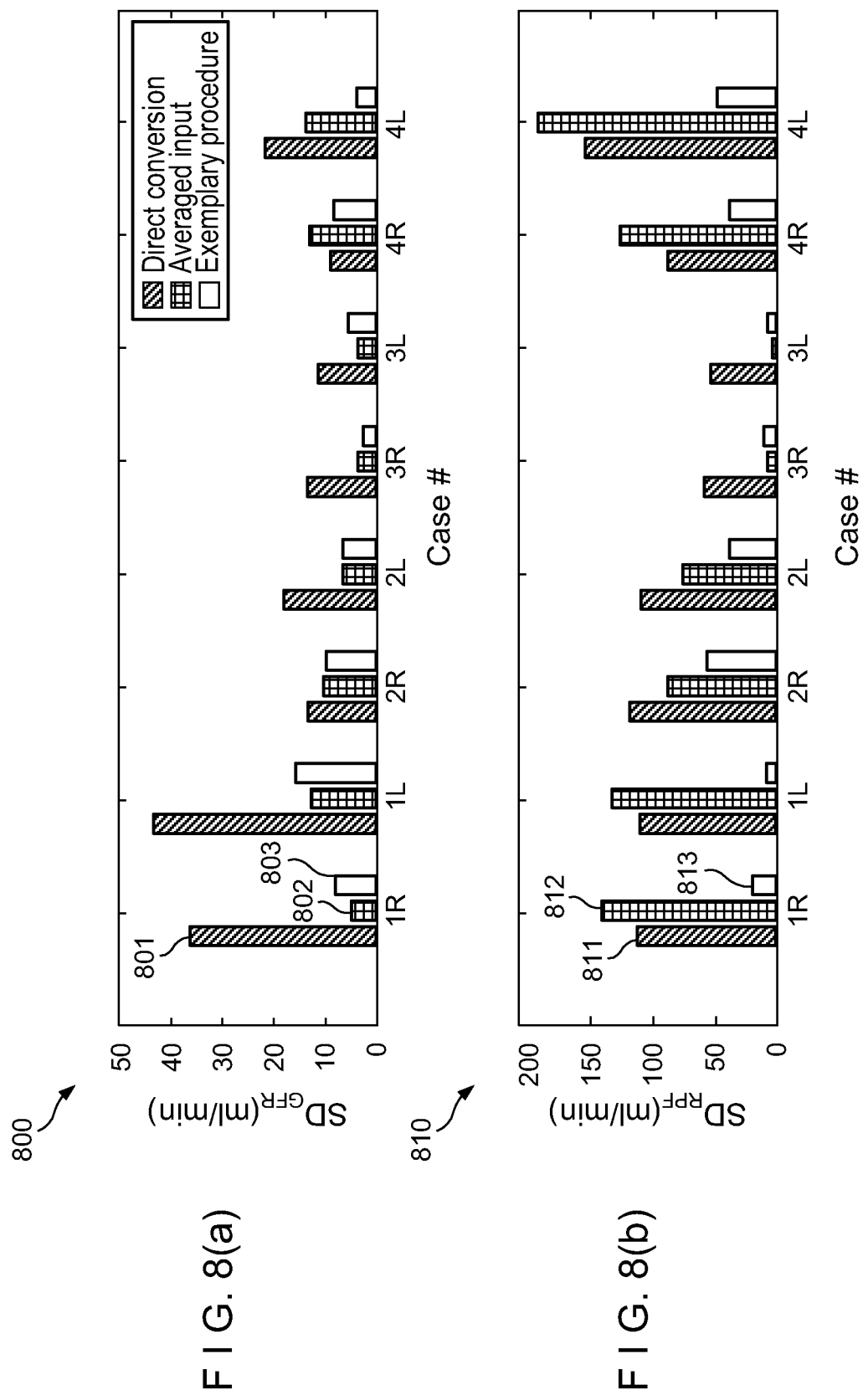
FIGS. 8(a) and 8(b) are illustrations of exemplary graphs showing exemplary standard deviations of three determinations for GFR and RPF, respectively, from three independent scans in four patients, in accordance with certain exemplary embodiments of the present disclosure.

FIGS. 8(a) and 8(b) illustrate exemplary graphs 800, 810 showing exemplary standard deviations (SD) of three determinations for GFR and RPF, respectively, from three independent scans in four patients, e.g., right kidney (R) and left kidney (L). As shown in this example by bars 803, 813, which represent results of the exemplary procedures according to the present disclosure, such exemplary procedures can result in a lower standard deviation for both GFR and RPF, as compared to direct conversion and/or averaged AIF procedures, the results of which are represented by bars 801, 811 and 802, 812, respectively.

Figure 9:
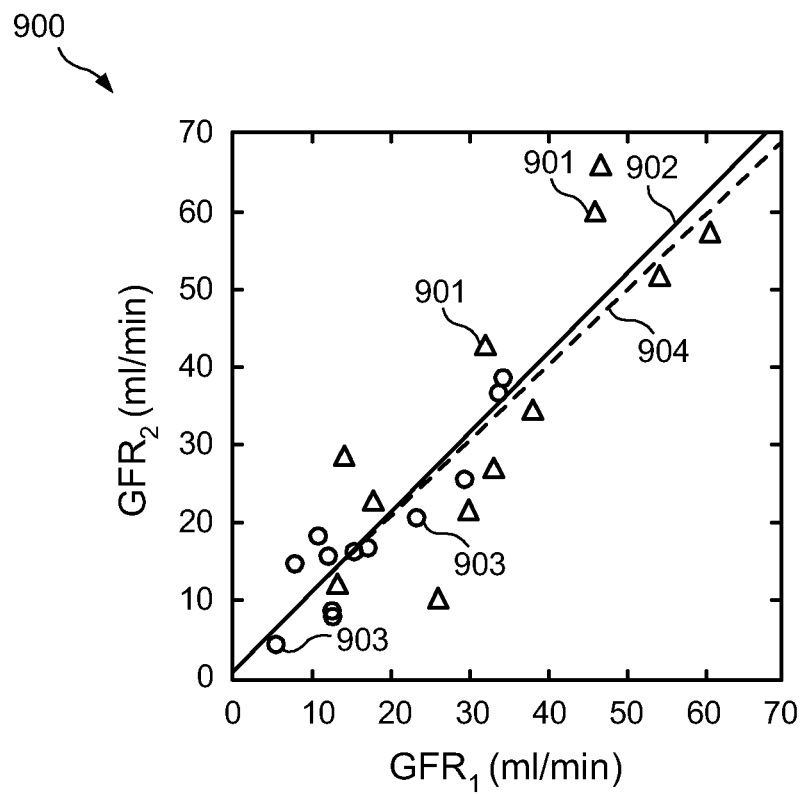
FIG. 9 is an illustration of an exemplary graph showing a comparison of a baseline GFR and second injection GFR for an example showing the reproducibility of GFR measured and/or determined within a single session, in accordance with certain exemplary embodiments of the present disclosure.

FIG. 9 illustrates an exemplary graph showing a comparison of a baseline GFR ($GFR_1$) and second injection GFR ($GFR_2$) for an example showing the reproducibility of GFR measured within a single session. For example, the cardiac output measurements for patients by phase-contrast MRI were about 4.7±1.2 L/min with a range of about 3.3-6.6 L/min. Exemplary results using a direct measurement procedure are represented by triangles 901. As shown in FIG. 9, using the exemplary direct measurement procedure, the correlation coefficient (R) between $GFR_1$ and $GFR_2$ can be about 0.83, with a regression line 902 of $GFR_2=1.03\ GFR_1+0.21$. In comparison, the exemplary procedure according to certain exemplary embodiments of the present disclosure can provide certain results, represented by circles 903, that can increase R to 0.92, with a regression line 904 of, e.g., $GFR_2=0.98\ GFR_1+0.57$.

Figure 10:
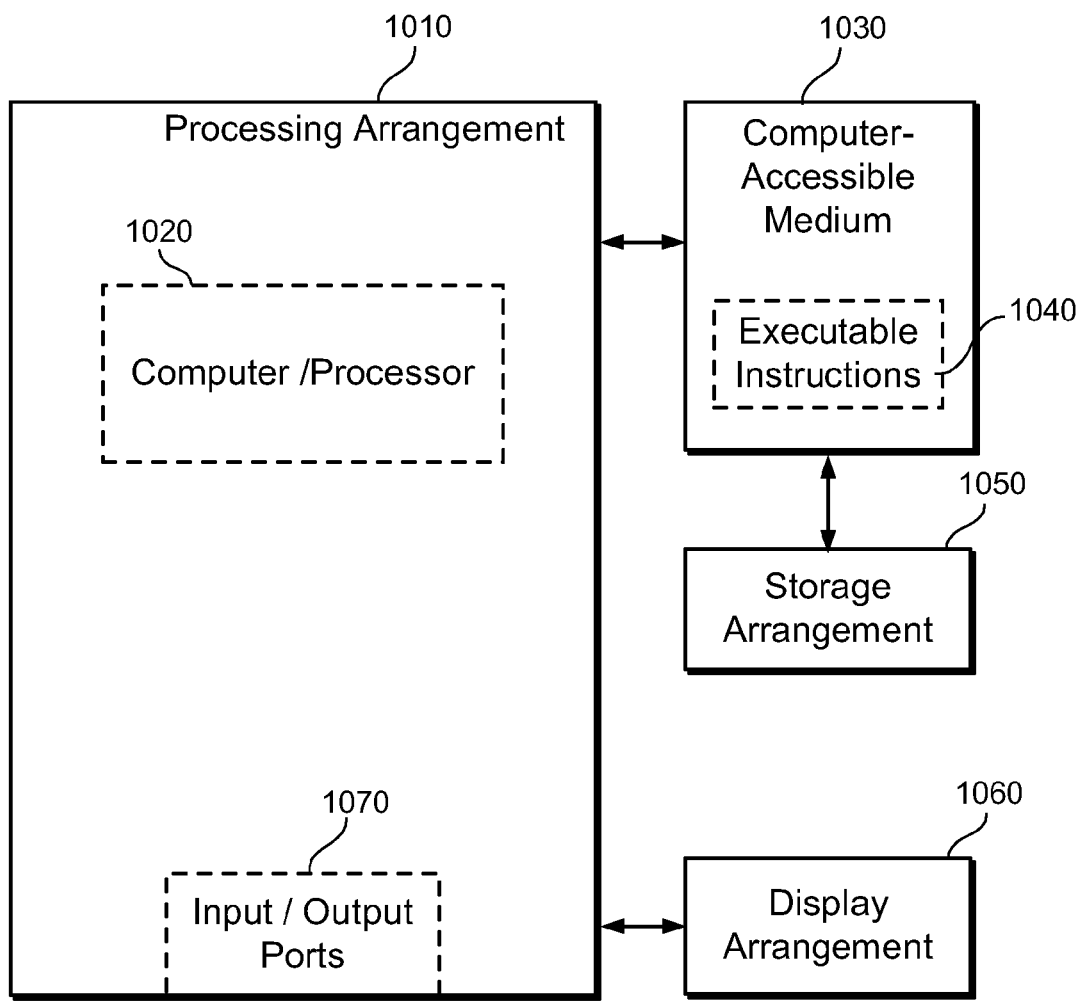
FIG. 10 is an illustration of an exemplary block diagram of an exemplary system, in accordance with certain exemplary embodiments of the present disclosure.

FIG. 10 shows an exemplary block diagram of an exemplary embodiment of a system according to the present disclosure. For example, an exemplary procedure in accordance with the present disclosure can be performed by a processing arrangement and/or a computing arrangement 1010. Such processing/computing arrangement 1010 can be, e.g., entirely or a part of, or include, but not limited to, a computer/processor 1020 that can include, e.g., one or more hardware processors and/or microprocessors, and use instructions stored on a computer-accessible medium (e.g., RAM, ROM, hard drive, or other storage device).

As shown in FIG. 10, e.g., a computer-accessible medium 1030 (e.g., as described herein above, a storage device such as a hard disk, floppy disk, memory stick, CD-ROM, RAM, ROM, etc., or a collection thereof) can be provided (e.g., in communication with the processing arrangement 1010). The computer-accessible medium 1030 can contain executable instructions 1040 thereon. In addition or alternatively, a storage arrangement 1050 can be provided separately from the computer-accessible medium 1030, which can provide the instructions to the processing arrangement 1010 so as to configure the processing arrangement to execute certain exemplary procedures, processes and methods, as described herein above, for example.

Further, the exemplary processing arrangement 1010 can be provided with or include an input/output arrangement 1070, which can include, e.g., a wired network, a wireless network, the internet, an intranet, a data collection probe, a sensor, etc. As shown in FIG. 10, the exemplary processing arrangement 1010 can be in communication with an exemplary display arrangement 1060, which, according to certain exemplary embodiments of the present disclosure, can be a touch-screen configured for inputting information to the processing arrangement in addition to outputting information from the processing arrangement, for example. Further, the exemplary display 1060 and/or a storage arrangement 1050 can be used to display and/or store data in a user-accessible format and/or user-readable format.

FIG. 11 shows a flow diagram of a procedure in accordance with certain exemplary embodiments of the present disclosure. As shown in FIG. 11, the exemplary procedure can be executed on and/or by, e.g., the processing/computing arrangement 1010. For example, starting at subprocess 1101, the exemplary procedure can, in subprocess 1102, obtain time sequence signal data. In subprocess 1130, the exemplary procedure can identify a first pass component of the time sequence signal data. Then, in subprocess 1104, the exemplary procedure can modify the time sequence signal data as a function of a corresponding first pass component and cardiac output data. Further, the exemplary procedure can, in subprocess 1105, generate the tracer concentration data using the modified time sequence signal data.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and methods which, although not explicitly shown or described herein, embody the principles of the disclosure and are thus within the spirit and scope of the disclosure. In addition, all publications and references referred to above are incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement and/or computing arrangement which can be and/or include a hardware processors, microprocessor, mini, macro, mainframe, etc., including a plurality and/or combination thereof. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words are intended to not be used synonymously. Further, to the extent that the prior art knowledge has not been explicitly incorporated by reference herein above, it is explicitly being incorporated herein in its entirety. All publications referenced above are incorporated herein by reference in their entireties.

What is claimed is:

1. A non-transitory computer-accessible medium having instructions thereon for generating tracer concentration data associated with a structure, wherein, when a computing arrangement executes the instructions, the computing arrangement, including a computer, is configured to perform procedures comprising:

activating at least one dynamic contrast enhanced (DCE) magnetic resonance imaging (MRI) scan;

generating, based on the DCE MRI scan, (i) cardiac output data associated with the structure, and (ii) time sequence signal data;

modifying the time sequence signal data using the cardiac output data under a constraint that a resulting concentration data generated from the modified time sequence signal data satisfies an indicator dilution principle; and generating the tracer concentration data using the modified time sequence signal data.

2. The computer-accessible medium of claim 1, wherein the computing arrangement is further configured to identify a first pass component of the time sequence signal data, and wherein the resulting tracer concentration data satisfies the indicator dilution principle within the first pass component.

3. The computer-accessible medium of claim 2, wherein the computing arrangement is further configured to generate a baseline signal level at least in part based on the first pass component.

4. The computer-accessible medium of claim 3, wherein the computing arrangement is further configured to generate time sequence concentration data as a function of at least one of (i) the time sequence signal data, (ii) the baseline signal level, or (iii) the cardiac output data.

5. The computer-accessible medium of claim 4, wherein the time sequence concentration data is generated to satisfy a constraint based on the indicator dilution principle.

6. The computer-accessible medium of claim 4, wherein the computing arrangement is further configured to obtain an initial time sequence signal data pertaining to the structure from a particular source, and the generation of the time sequence concentration data is performed by modifying the initial time sequence signal data as a function of the generated baseline signal level.

7. The computer-accessible medium of claim 4, wherein the baseline signal level is determined based on (i) an area under the curve corresponding to the tracer concentration data associated with the first pass component of signal data, (ii) a mass of a tracer injected into the structure, and (iii) the cardiac output data.

8. The computer-accessible medium of claim 4, wherein the time sequence concentration data is generated as a function of the baseline signal level, the time sequence signal data, and the cardiac output data;

the time sequence signal data is generated based on data associated with a region of interest pertaining to an artery; and the generation of the time sequence concentration data is performed using an indicator dilution principle.

9. The computer-accessible medium of claim 3, wherein the computing arrangement is further configured to determine the first pass component of signal data by fitting the time sequence signal data to a gamma variate function.

10. The computer-accessible medium of claim 9, wherein the computing arrangement is further configured to generate a time sequence concentration data that includes shifting values of the time sequence signal data.

11. The computer-accessible medium of claim 1, wherein the tracer concentration is generated data using a direct measurement method.

12. The computer-accessible medium of claim 1, wherein the tracer concentration data corresponds to an arterial input function.

13. A system for generating tracer concentration data associated with a structure, comprising:

a non-transitory computer-accessible medium having executable instructions thereon, wherein when at least one computing arrangement executes the instructions, the at least one computing arrangement, including a computer, is configured to:

activate at least one dynamic contrast enhanced (DCE) magnetic resonance imaging (MRI) scan;

generate, based on the DCE MRI scan, (i) cardiac output data associated with the structure, and (ii) time sequence signal data;

modify the time sequence signal data using the cardiac output data under a constraint that a resulting tracer concentration generated from the modulated time sequence signal data satisfies an indicator dilution principle; and generate the tracer concentration data using the modified time sequence signal data.

14. The system of claim 13, wherein the computing arrangement is further configured to identify a first pass component of the time sequence signal data, and wherein the resulting tracer concentration data satisfies the indicator dilution principle within a corresponding first pass component.

15. A non-transitory computer-accessible medium having instructions thereon for generating tracer concentration data associated with a structure, wherein, when a computing arrangement executes the instructions, the computing arrangement, including a computer, is configured to perform procedures comprising:

activating at least one dynamic contrast enhanced (DCE) magnetic resonance imaging (MRI) scan;

generating, based on the DCE MRI scan, (i) cardiac output data associated with the structure, and (ii) time sequence signal data;

modifying the time sequence signal data as a function of a corresponding first pass component using the cardiac output data; and generating the tracer concentration data using the modified time sequence signal data.

16. The computer-accessible medium of claim 15, wherein the computing arrangement is further configured to generate time sequence concentration data as a function of (i) the time sequence signal data, (ii) a baseline signal level, and (iii) the cardiac output data.

17. The computer-accessible medium of claim 16, wherein the time sequence concentration data is generated to satisfy a constraint based on the indicator dilution principle.

18. The computer-accessible medium of claim 16, wherein the computing arrangement is further configured to obtain an initial time sequence signal data pertaining to the structure from a particular source, and the generation of the time sequence concentration data is performed by modifying the initial time sequence signal data as a function of a baseline signal level.

19. The computer-accessible medium of claim 16, wherein the computing arrangement is further configured to determine the first pass component of signal data by fitting the time sequence signal data to a gamma variate function.

20. The computer-accessible medium of claim 16, wherein the baseline signal level is determined based on (i) an area under the curve corresponding to the tracer concentration data associated with a corresponding first pass (ii) a mass of a tracer injected into the structure, and (iii) the cardiac output data.

21. The computer-accessible medium of claim 16, wherein the generation of the time sequence signal data includes shifting values of the time sequence signal data.

22. The computer-accessible medium of claim 16, wherein
the time sequence concentration data is generated as a function of a baseline signal level, the time sequence signal data, and the cardiac output data;
the time sequence signal data is generated based on data associated with a region of interest pertaining to an artery; and
the generation of the time sequence concentration data is performed using an indicator dilution principle.

23. The computer-accessible medium of claim 15, wherein the time sequence signal data is converted to the tracer concentration data using a direct measurement method.

24. The computer-accessible medium of claim 15, wherein the tracer concentration data corresponds to an arterial input function.

25. A system for generating tracer concentration data associated with a structure, comprising:

a non-transitory computer-accessible medium having executable instructions thereon, wherein when at least one computing arrangement executes the instructions, the at least one computing arrangement, including a computer, is configured to:

generate a baseline signal level based at least in part on a first pass signal data;

activate at least one dynamic contrast enhanced (DCE) magnetic resonance imaging (MRI) scan;

generate (i) cardiac output data based on the DCE MRI scan, and (ii) time sequence signal data as a function of the generated baseline signal level using the cardiac output data and the DCE MRI scan; and generate the tracer concentration data as a function of the generated time sequence signal data.

26. A method for generating tracer concentration data associated with a structure, comprising:

activating at least one dynamic contrast enhanced (DCE) magnetic resonance imaging (MRI) scan;

generating, based on the DCE MRI scan, (i) cardiac output data associated with the structure, and (ii) time sequence signal data;

modifying the time sequence signal data using the cardiac output data under a constraint that a resulting tracer concentration data generated from the modified time sequence signal data satisfies an indicator dilution principle; and using a computer hardware arrangement, generating the tracer concentration data using the modified time sequence data.

27. The method of claim 26, further comprising injecting at least one contrast agent into a patient associated with the structure.

* * * * *